(12) United States Patent
Takemoto et al.

(10) Patent No.: US 7,556,908 B2
(45) Date of Patent: Jul. 7, 2009

(54) CHEMICALLY AMPLIFIED POSITIVE RESIST COMPOSITION, (METH)ACRYLATE DERIVATIVE AND A PROCESS FOR PRODUCING THE SAME

(75) Inventors: Ichiki Takemoto, Kawanishi (JP); Isao Yoshida, Ikeda (JP); Takayuki Miyagawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/110,763

(22) Filed: Apr. 21, 2005

(65) Prior Publication Data

US 2005/0266351 A1    Dec. 1, 2005

(30) Foreign Application Priority Data

Apr. 23, 2004 (JP) .............. 2004-128093
Feb. 25, 2005 (JP) .............. 2005-050664

(51) Int. Cl.
*G03F 7/039* (2006.01)
*G03F 7/004* (2006.01)
*H01L 21/027* (2006.01)
*C23F 1/00* (2006.01)

(52) U.S. Cl. .............. 430/270.1; 430/921; 430/914; 522/31

(58) Field of Classification Search .............. None
See application file for complete search history.

(56) References Cited

U.S. PATENT DOCUMENTS

| | | | | |
|---|---|---|---|---|
| 6,479,211 | B1 * | 11/2002 | Sato et al. .............. | 430/270.1 |
| 7,439,006 | B2 * | 10/2008 | Yoshida et al. .......... | 430/270.1 |
| 2003/0054286 | A1 | 3/2003 | Sato et al. | |
| 2003/0180663 | A1 * | 9/2003 | Namba et al. ............ | 430/270.1 |
| 2003/0219680 | A1 | 11/2003 | Nishimura et al. | |
| 2005/0130058 | A1 * | 6/2005 | Rahman .................. | 430/270.1 |
| 2007/0027336 | A1 * | 2/2007 | Yoshida et al. .............. | 560/129 |
| 2007/0078269 | A1 * | 4/2007 | Harada et al. ............... | 549/266 |
| 2007/0249192 | A1 * | 10/2007 | Tsurumi ..................... | 439/94 |
| 2008/0081293 | A1 * | 4/2008 | Harada et al. ............ | 430/287.1 |

FOREIGN PATENT DOCUMENTS

JP    11-218924 A    8/1999
JP    2003-147019 A    5/2003

OTHER PUBLICATIONS

Takemoto et al., Proceedings of SPIE, vol. 5753, pp. 584-591, (2005), May.

* cited by examiner

*Primary Examiner*—Cynthia Hamilton
(74) *Attorney, Agent, or Firm*—Birch, Stewart, Kolasch & Birch, LLP

(57) ABSTRACT

The present invention provides a chemically amplified positive resist composition comprising
(A) a resin which comprises
(i) a structural unit of the formula (I) and
(ii) at least one structural unit selected from the group consisting of structural units of the formulas (II), (O/II), (IV) and (V) and
(B) an acid generator.

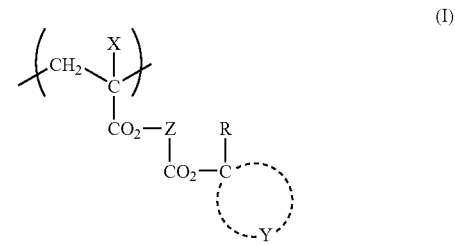

(I)

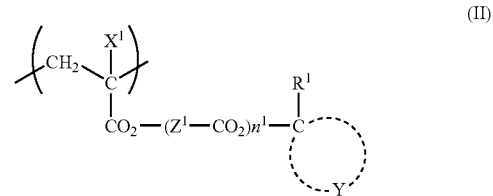

(II)

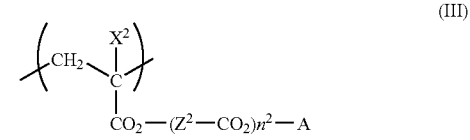

(III)

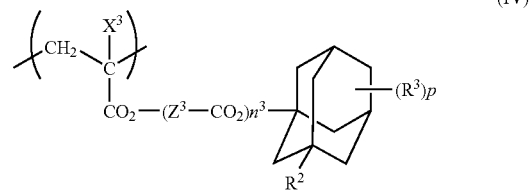

(IV)

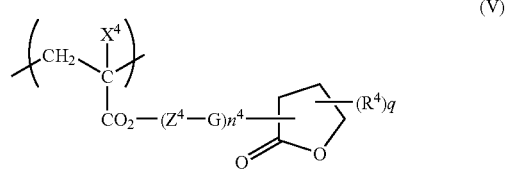

(V)

The present invention further provides a novel monomers useful for the resist composition, and process for the monomers and the compositions.

2 Claims, No Drawings

CHEMICALLY AMPLIFIED POSITIVE RESIST COMPOSITION, (METH)ACRYLATE DERIVATIVE AND A PROCESS FOR PRODUCING THE SAME

This nonprovisional application claims priority under 35 U.S.C. § 119(a) on Patent Application Nos. 2004-128093 and 2005-050664 filed in JAPAN on Apr. 23, 2004 and Feb. 25, 2005, the entire contents of which are hereby incorporated by reference.

BACKGROUND OF THE INVENTION

1. Field of the Invention

The present invention relates to a chemically amplified positive resist composition used in fine processing of semiconductors, a component resin in the composition, a (meth) acrylic derivative for the component resin and a process for producing the (meth)acrylic derivative.

2. Related Art

Semiconductor microfabrication employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be the next-generation exposure light source. Further, as the exposure light source of the subsequent generation, soft X ray (EUV) having a wavelength of 13 nm or shorter has been proposed as the exposure light source following the 157 nm-wavelength $F_2$ excimer laser.

As line width has become narrower in lithography process using light sources having shorter wavelength, such as excimer laser and the like, especially line edge roughness (roughness of pattern surfaces or wave of pattern, abbreviated by LER), as well as resolution, sensitivity and pattern shape, has become important subject (e.g. Proc. of SPIE Vol. 5038 (2003), 689-698).

After forming patterns by application of the resist composition, exposure of light, and development, there exists a technique adding a step narrowing width of hollows and diameter of holes to make patterns finer by high temperature baking to swell the resist (e.g. JP-A-H09-213603). Hereinafter, the step described above may be referred to as "Reflow Step".

With further advance of microfabrication technology, it is required for new photoresist compositions to show more advantageous abilities than conventional photoresists. Specifically, photoresist compositions giving better resolution, sensitivity, pattern profiles to resist pattern obtained therefrom, especially giving better line edge roughness are required. Under certain circumstances, further, photoresist compositions capable of giving finer patterns by Reflow Step are required.

SUMMARY OF THE INVENTION

An object of the present invention is to provide a chemically amplified resist composition suitable for excimer laser lithography using ArF, KrF and the like, showing excellent various resist abilities, and giving particularly excellent line edge roughness, and capable of giving finer patterns by Reflow Step.

Another object of the present invention is to provide a new resin used as a component in the resist composition above.

Still another object of the present invention is to provide new (meth)acrylic derivatives useful for the component resin in the resist composition above.

Yet another object of the present invention is to provide a production method for the new (meth)acrylic derivatives thereof.

These and other objects of the present invention will be apparent from the following description.

The present invention relates to the followings:

<1> A chemically amplified positive resist composition comprising (A) a resin which comprises (i) a structural unit of the formula (I)

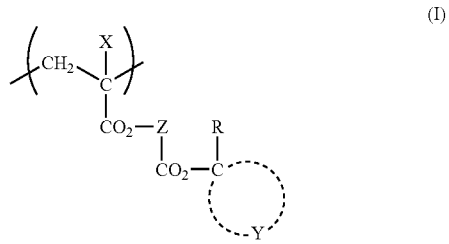

wherein X represents a hydrogen atom, an alkyl group having 1 to 4 carbon atoms or a perfluoroalkyl group having 1 to 4 carbon atoms, Y represents at least two atoms necessary to form an alicyclic hydrocarbon group together with the adjacent carbon atom, Z represents a divalent hydrocarbon group having 1 to 12 carbon atoms, R represents an alkyl group having 1 to 6 carbon atoms or an alicyclic hydrocarbon group having 3 to 12 carbon atoms and (ii) at least one structural unit selected from the group consisting of structural units of the formulas (II), (III), (IV) and (V)

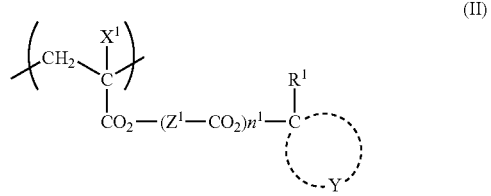

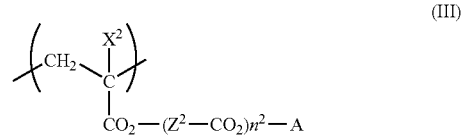

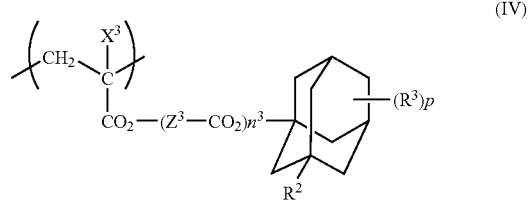

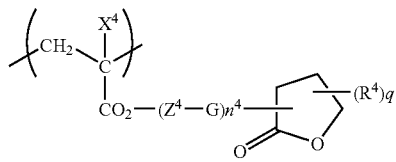
(V)

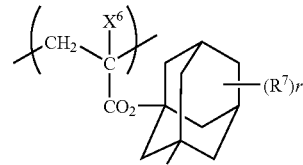
(VII)

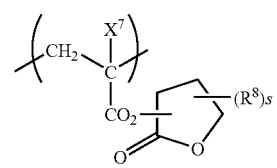
(VIII)

wherein $X^1$, $X^2$, $X^3$ and $X^4$ each independently represents a hydrogen atom, an alkyl group having 1 to 4 carbon atoms or a perfluoroalkyl group having 1 to 4 carbon atoms, $Z^1$, $Z^2$, $Z^3$ and $Z^4$ each independently represents a divalent hydrocarbon group having 1 to 12 carbon atoms, $n^1$, $n^2$, $n^3$ and $n^4$ each independently represents an integer of 0 to 3, $R^1$ represents an alkyl group having 1 to 6 carbon atoms or a cycloalkyl group having 3 to 12 carbon atoms, A represents a hydrocarbon group having 1 to 12 carbon atoms, $R^2$ and $R^3$ each independently represents a hydroxyl group or a hydroxymethyl group, G represents —(CO)O— or —O—, $R^4$ represents an alkyl group having 1 to 4 carbon atoms or an alkoxy group having 1 to 4 carbon atoms, p and q each independently represents an integer of 0 to 2, and Y has the same meaning as defined above, with the proviso that each of the structural units of the formulas (II) and (III) is different from the structural unit of the formula (I), and (B) an acid generator.

<2> The composition according to <1>, wherein the structural unit of the formula (I) is a structural unit of the formula (VI)

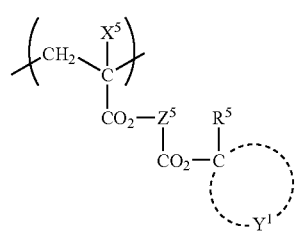
(VI)

wherein $X^5$ represents a hydrogen atom, an alkyl group having 1 to 4 carbon atoms or a perfluoroalkyl group having 1 to 4 carbon atoms, $Y^1$ represents at least two atoms necessary to form an alicyclic hydrocarbon group having 2 to 12 carbon atoms together with the adjacent carbon atom, $Z^5$ represents a divalent hydrocarbon group having 1 to 12 carbon atoms, $R^5$ represents an alkyl group having 1 to 6 carbon atoms or an alicyclic hydrocarbon group having 3 to 12 carbon atoms, and at least one structural unit selected from the group consisting of the structural units of the formulas (II), (III), (IV) and (V) is at least one structural unit selected from the group consisting of the structural units of the formulas (III), (VII) and (VIII)

wherein $X^6$ and $X^7$ each independently represents a hydrogen atom, an alkyl group having 1 to 4 carbon atoms or a perfluoroalkyl group having 1 to 4 carbon atoms, $R^6$ and $R^7$ each independently represents a hydroxy group or a hydroxymethyl group, $R^8$ represents an alkyl group having 1 to 4 carbon atoms or an alkoxy group having 1 to 4 carbon atoms, r and s each independently represents an integer of 0 to 2.

<3> The composition according to <2>, wherein the structural unit of the formula (VI) is a structural unit of the formula (IX)

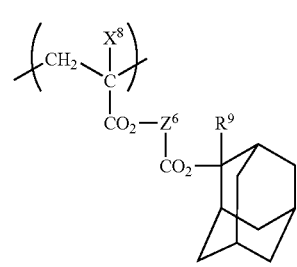
(IX)

wherein $X^8$ represents a hydrogen atom, an alkyl group having 1 to 4 carbon atoms or a perfluoroalkyl group having 1 to 4 carbon atoms, $Z^6$ represents a methylene group, an ethylene group, a trimethylene group or a tetramethylene group, and $R^9$ represents an alkyl group having 1 to 4 carbon atoms, and at least one structural unit selected from the group consisting of the structural units of the formulas (III), (VII) and (VIII) is at least one structural unit selected from the group consisting of the structural units of the formulas (VII) and (VIII).

<4> The composition according to <3>, wherein the structural unit of the formula (IX) is a structural unit of the formula (X)

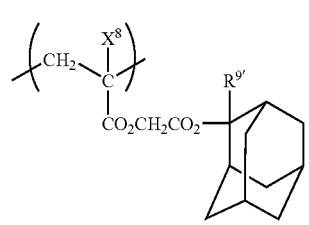
(X)

wherein $X^8$ represents a hydrogen atom or a methyl group, and $R^9$ represents a methyl group, an ethyl group, isopropyl group or a butyl group, and at least one structural unit selected from the group consisting of the structural units of the formulas (VII) and (VIII) is at least one structural unit selected from the group consisting of structural units of the formulas (XI) and (VIII')

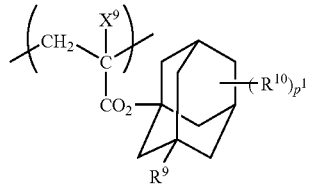

(XI)

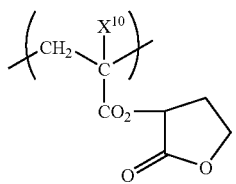

(VIII')

wherein $X^9$ and $X^{10}$ each independently represents a hydrogen atom or a methyl group, $R^9$ and $R^{10}$ each independently represents a hydroxy group or a hydroxymethyl group, and $p^1$ represents 0 or 1.

<5> A (meth)acrylic derivative of the formula (XII)

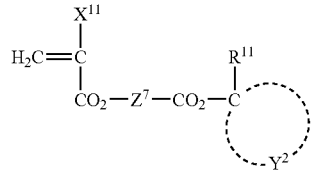

(XII)

wherein $X^{11}$ represents a hydrogen atom, a methyl group or a trifluoromethyl group; (1) $R^{11}$ represents a methyl group, $Y^2$ represents a divalent hydrocarbon group which forms an adamantane skeleton together with the adjacent carbon atom, and $Z^7$ represents a methylene group, a trimethylene group or a tetramethylene group, (2) $R^{11}$ represents an ethyl group, an isopropyl group or a butyl group, $Y^2$ represents a divalent hydrocarbon group which forms an adamantane skeleton together with the adjacent carbon atom, and $Z^7$ represents a methylene group, an ethylene group, a trimethylene group or a tetramethylene group, or (3) $R^{11}$ represents a methyl group, an ethyl group, an isopropyl group or a butyl group, $Y^2$ represents a tetramethylene group, a pentamethylene group or a divalent hydrocarbon group which forms a norbornane skeleton together with the adjacent carbon atom, and $Z^7$ represents a methylene group, an ethylene group, a trimethylene group or a tetramethylene group.

<6> A (meth)acrylic derivative of the formula (XIII)

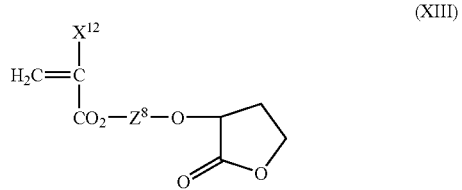

(XIII)

wherein $X^{12}$ represents a hydrogen atom, a methyl group or a trifluoromethyl group, $Z^8$ represents an ethylene group, trimethylene group, a tetramethylene group, a methylcarbonyl group, an ethylcarbonyl group, a propylcarbonyl group or a butylcarbonyl group.

<7> A (meth)acrylic derivative of the formula (XIV)

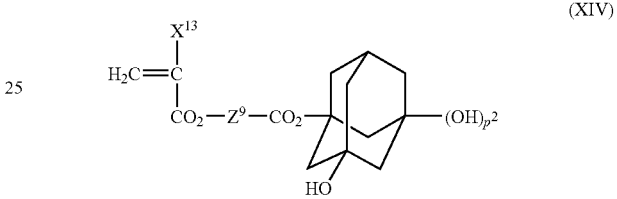

(XIV)

wherein $X^{13}$ represents a hydrogen atom, a methyl group or a trifluoromethyl group, $Z^9$ represents a methylene group, an ethylene group, trimethylene group or a tetramethylene group and $p^2$ represents 0 or 1.

<8> A process for producing a (meth)acrylic derivative of the formula (XII)

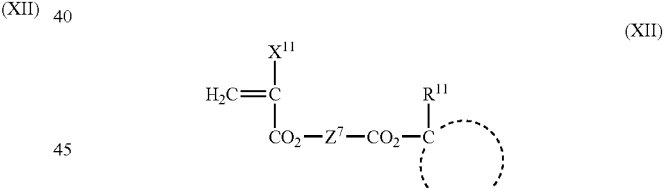

(XII)

wherein $X^{11}$ represents a hydrogen atom, a methyl group or a trifluoromethyl group; (1) $R^{11}$ represents a methyl group, $Y^2$ represents a divalent hydrocarbon group which forms an adamantane skeleton together with the adjacent carbon atom, and $Z^7$ represents a methylene group, a trimethylene group or a tetramethylene group, (2) $R^{11}$ represents an ethyl group, an isopropyl group or a butyl group, $Y^2$ represents a divalent hydrocarbon group which forms an adamantane skeleton together with the adjacent carbon atom, and $Z^7$ represents a methylene group, an ethylene group, a trimethylene group or a tetramethylene group, or (3) $R^{11}$ represents a methyl group, an ethyl group, an isopropyl group or a butyl group, $Y^2$ represents a tetramethylene group, a pentamethylene group or a divalent hydrocarbon group which forms a norbornane skeleton together with the adjacent carbon atom, and $Z^7$ represents a methylene group, an ethylene group, a trimethylene group or a tetramethylene group, which comprises reacting an alcohol derivative of the formula (XV)

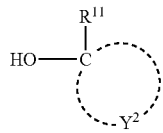
(XV)

wherein $R^{11}$ and $Y^2$ have the same meanings as defined above, with the proviso that the correlation between $R^{11}$, $Y^2$ and $Z^7$ in the formula (XII) is maintained, with an acid halide derivative of the formula (XVI) to obtain a condensate $$W^1\text{-}Z^7\text{-}CO\text{—}W^2 \quad \text{(XVI)}$$

wherein $W^1$ and $W^2$ each independently represents a chlorine atom, a bromine atom or an iodine atom, and $Z^7$ has the same meaning as defined above, with the proviso that the correlation between $R^{11}$, $Y^2$ and $Z^7$ in the formula (XII) is maintained, and reacting the condensate with a carboxylic acid of the formula (XVII)

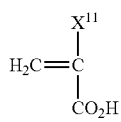
(XVII)

wherein $X^{11}$ has the same meaning as defined above, in the presence of a deacidifying agent.

<9> A process for producing a (meth)acrylic derivative of the formula (XIII)

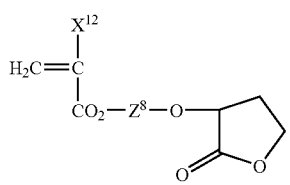
(XIII)

wherein $X^{12}$ represents a hydrogen atom, a methyl group or a trifluoromethyl group, $Z^8$ represents an ethylene group, trimethylene group, a tetramethylene group, a methylcarbonyl group, an ethylcarbonyl group, a propylcarbonyl group or a butylcarbonyl group, which comprises reacting a γ-butyrolactone derivative of the formula (XVIII)

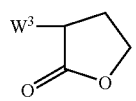
(XVIII)

wherein $W^3$ represents a chlorine atom, a bromine atom or an iodine atom, with a hydroxy derivative of the formula (XIX)

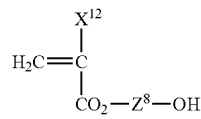
(XIX)

wherein $X^{12}$ and $Z^8$ have the same meanings as defined above, in the presence of a deacidifying agent.

<10> A process for producing an acrylic derivative of the formula (XIV)

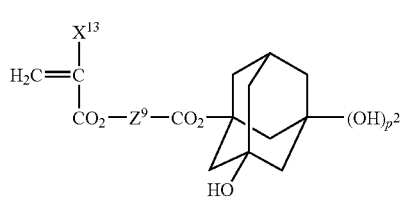
(XIV)

wherein $X^{13}$ represents a hydrogen atom, a methyl group or a trifluoromethyl group, $Z^9$ represents a methylene group, an ethylene group, trimethylene group or a tetramethylene group and $p^2$ represents 0 or 1, which comprises reacting a hydroxyadamantane derivative of the formula (XX)

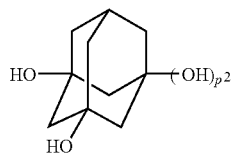
(XX)

wherein $p^2$ has the same meaning as defined above, with a carboxylic acid derivative of the formula (XXI)

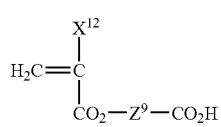
(XXI)

wherein $X^{12}$ and $Z^9$ have the same meanings as defined above, in the presence of a deacidifying agent.

<11> A (meth)acrylic resin which has an weight average molecular weight of 1000 to 500000, and which comprises (i) a structural unit of the formula (XII')

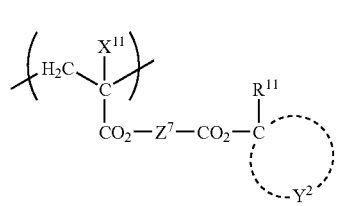
(XII')

wherein $X^{11}$ represents a hydrogen atom, a methyl group or a trifluoromethyl group; (1) $R^{11}$ represents a methyl group, $Y^2$ represents a divalent hydrocarbon group which forms an adamantane skeleton together with the adjacent carbon atom, and $Z^7$ represents a methylene group, a trimethylene group or a tetramethylene group, (2) $R^{11}$ represents an ethyl group, an isopropyl group or a butyl group, $Y^2$ represents a divalent hydrocarbon group which forms an adamantane skeleton together with the adjacent carbon atom, and $Z^7$ represents a methylene group, an ethylene group, a trimethylene group or a tetramethylene group, or (3) $R^{11}$ represents a methyl group, an ethyl group, an isopropyl group or a butyl group, $Y^2$ represents a tetramethylene group, a pentamethylene group or a divalent hydrocarbon group which forms a norbornane skeleton together with the adjacent carbon atom, and $Z^7$ represents a methylene group, an ethylene group, a trimethylene group or a tetramethylene group, and (ii) at least one structural unit selected from the group consisting of structural units of the formulas (II), (III), (IV) and (V)

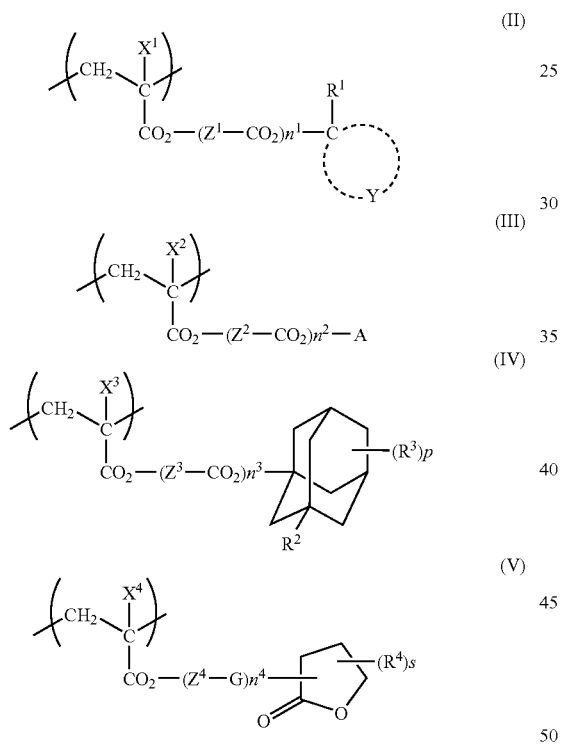

wherein $X^1$, $X^2$, $X^3$ and $X^4$ each independently represents a hydrogen atom, an alkyl group having 1 to 4 carbon atoms or a perfluoroalkyl group having 1 to 4 carbon atoms, $Z^1$, $Z^2$, $Z^3$ and $Z^4$ each independently represents a divalent hydrocarbon group having 1 to 12 carbon atoms, $n^1$, $n^2$, $n^3$ and $n^4$ each independently represents an integer of 0 to 3, $R^1$ represents an alkyl group having 1 to 6 carbon atoms or a cycloalkyl group having 3 to 12 carbon atoms, A represents a hydrocarbon group having 1 to 12 carbon atoms, $R^2$ and $R^3$ each independently represents a hydroxyl group or a hydroxymethyl group, G represents —(CO)O— or —O—, $R^4$ represents an alkyl group having 1 to 4 carbon atoms or an alkoxy group having 1 to 4 carbon atoms, p and q each independently represents an integer of 0 to 2, and Y has the same meaning as defined above, with the proviso that each of the structural units of the formulas (II) and (III) is different from the structural unit of the formula (I).

<12> A (meth)acrylic resin which has an weight average molecular weight of 1000 to 500000, and which comprises (i) a structural unit of the formula (X)

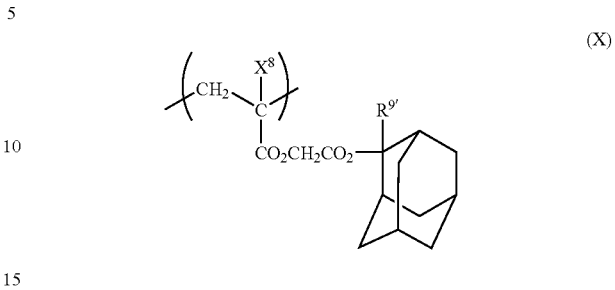

wherein $X^8$ represents a hydrogen atom or a methyl group, and $R^9$ represents a methyl group, an ethyl group, isopropyl group or a butyl group, and (ii) at least one structural unit selected from the group consisting of structural units of the formulas (II), (III), (IV) and (V)

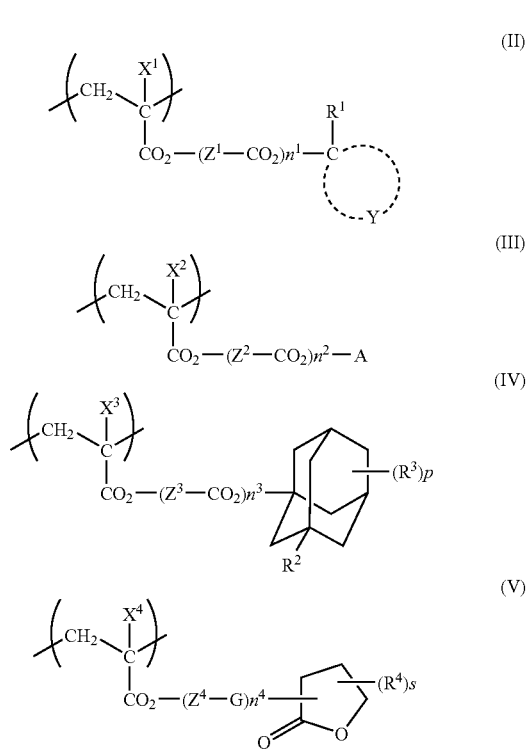

wherein $X^1$, $X^2$, $X^3$ and $X^4$ each independently represents a hydrogen atom, an alkyl group having 1 to 4 carbon atoms or a perfluoroalkyl group having 1 to 4 carbon atoms, $Z^1$, $Z^2$, $Z^3$ and $Z^4$ each independently represents a divalent hydrocarbon group having 1 to 12 carbon atoms, $n^1$, $n^2$, $n^3$ and $n^4$ each independently represents an integer of 0 to 3, $R^1$ represents an alkyl group having 1 to 6 carbon atoms or a cycloalkyl group having 3 to 12 carbon atoms, A represents a hydrocarbon group having 1 to 12 carbon atoms, $R^2$ and $R^3$ each independently represents a hydroxyl group or a hydroxymethyl group, G represents —(CO)O— or —O—, $R^4$ represents an alkyl group having 1 to 4 carbon atoms or an alkoxy group having 1 to 4 carbon atoms, p and q each independently represents an integer of 0 to 2, and Y has the same meaning as defined above, with the proviso that each of the structural units of the formulas (II) and (III) is different from the structural unit of the formula (I).

<13> A process for producing a (meth)acrylic resin comprising radical-polymerizing, anion-polymerizing or coordination-polymerizing a (meth)acrylic derivative of the formulas (X') or (XII)

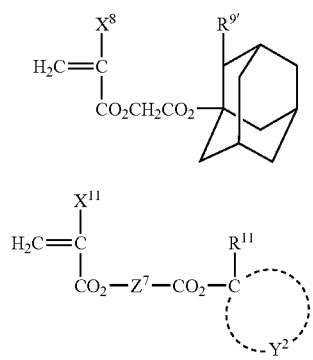

(X')

(XII)

wherein $X^8$ and $X^{11}$ each independently represents a hydrogen atom, a methyl group or a trifluoromethyl group; $R^{9'}$ represents a methyl group, an ethyl group, an isopropyl group or a butyl group; (1) $R^{11}$ represents a methyl group, $Y^2$ represents a divalent hydrocarbon group which forms an adamantane skeleton together with the adjacent carbon atom, and $Z^7$ represents a methylene group, a trimethylene group or a tetramethylene group, (2) $R^{11}$ represents an ethyl group, an isopropyl group or a butyl group, $Y^2$ represents a divalent hydrocarbon group which forms an adamantane skeleton together with the adjacent carbon atom, and $X^7$ represents a methylene group, an ethylene group, a trimethylene group or a tetramethylene group, or (3) $R^{11}$ represents a methyl group, an ethyl group, an isopropyl group or a butyl group, $Y^2$ represents a tetramethylene group, a pentamethylene group or a divalent hydrocarbon group which forms a norbornane skeleton together with the adjacent carbon atom, $Z^7$ represents a methylene group, an ethylene group, a trimethylene group or a tetramethylene group, with a (meth)acrylic derivative other than the (meth)acrylic derivatives of the formulas (XII) and (X').

DESCRIPTION OF PREFERRED EMBODIMENTS

The present composition is useful for a chemically amplified positive resist, and the composition comprises
(A) a resin which comprises
(i) a structural unit of the formula (I)

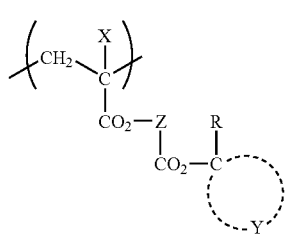

(I)

wherein X represents a hydrogen atom, an alkyl group having 1 to 4 carbon atoms or a perfluoroalkyl group having 1 to 4 carbon atoms, Y represents at least two atoms necessary to form an alicyclic hydrocarbon group together with the adjacent carbon atom, Z represents a divalent hydrocarbon group having 1 to 12 carbon atoms, R represents an alkyl group having 1 to 6 carbon atoms or an alicyclic hydrocarbon group having 3 to 12 carbon atoms and (ii) at least one structural unit selected from the group consisting of structural units of the formulas (II), (III), (IV) and (V)

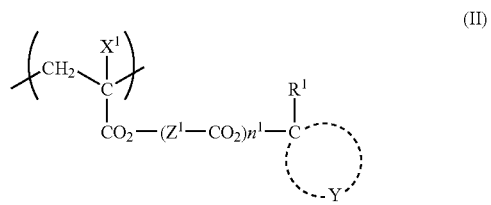

(II)

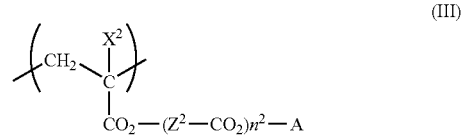

(III)

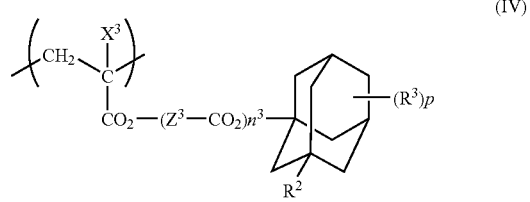

(IV)

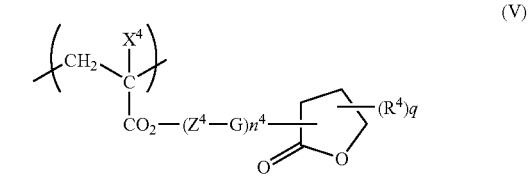

(V)

wherein $X^1$, $X^2$, $X^3$ and $X^4$ each independently represents a hydrogen atom, an alkyl group having 1 to 4 carbon atoms or a perfluoroalkyl group having 1 to 4 carbon atoms, $Z^1$, $Z^2$, $Z^3$ and $Z^4$ each independently represents a divalent hydrocarbon group having 1 to 12 carbon atoms, $n^1$, $n^2$, $n^3$ and $n^4$ each independently represents an integer of 0 to 3, $R^1$ represents an alkyl group having 1 to 6 carbon atoms or a cycloalkyl group having 3 to 12 carbon atoms, A represents a hydrocarbon group having 1 to 12 carbon atoms, $R^2$ and $R^3$ each independently represents a hydroxyl group or a hydroxymethyl group, G represents —(CO)O— or —O—, $R^4$ represents an alkyl group having 1 to 4 carbon atoms or an alkoxy group having 1 to 4 carbon atoms, p and q each independently represents an integer of 0 to 2, and Y has the same meaning as defined above, with the proviso that each of the structural units of the formulas (II) and (III) is different from the structural unit of the formula (I), and (B) an acid generator.

Hereinafter, "a resin which comprises (i) a structural unit of the formula (I) and (ii) at least one structural unit selected from the group consisting of structural units of the formulas (II), (III), (IV) and (V)" may be referred to as "RESIN".

RESIN itself is usually insoluble or poorly soluble in an alkali aqueous solution but becomes soluble in an alkali aqueous solution by the action of an acid. Specifically some group(s) in structural unit(s) constructing RESIN is (are) dissociated by an acid, and the resin component becomes soluble in an alkali aqueous solution after the dissociation.

In the structural unit of the formula (I), X represents a hydrogen atom; an alkyl group having 1 to 4 carbon atoms such as a methyl group, an ethyl group, and the like; or a perfluoroalkyl group having 1 to 4 carbon atoms such as a trifluoromethyl group, an pentafluoroethyl group, and the like. R represents an alkyl group having 1 to 6 carbon atoms such as a methyl group, an ethyl group, an isopropyl group, a n-butyl group, an isobutyl group, a sec-butyl group, a tert-butyl group, and the like; or an alicyclic hydrocarbon group having 3 to 12 carbon atoms such as a cyclopropyl group, a cyclobutyl group, a cyclopentyl group, a cyclohexyl group, a decahydronaphthyl group, a decahydro-1,4:5,8-dimethanonaphthyl group, and the like. Z represents a divalent hydrocarbon group having 1 to 12 carbon atoms, and examples thereof include alkylene groups such as a methylene group, ethylidene group, a propylidene group, and the like; polymethylene groups such as an ethylene group, a propylene group, a 1,2-butylene group, a trimethylene group, a tetramethylene group, a pentamethylene group, a hexamethylene group, a heptamethylene group, an octamethylene group, a dodecamethylene group, 1,1-dimethyltrimethylene group, a 1,1-dimethyltetramethylene group, and the like; groups shown by -Pm-Cy- such as

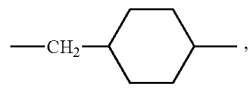

and the like, wherein Pm represents an optionally substituted (poly)methylene group having 1 to 4 carbon atoms and Cy represents a cycloalkan-diyl group having 3 to 8 carbon atoms.

Y represents at least two atoms necessary to form an alicyclic hydrocarbon group together with the adjacent carbon atom, in other words, Y represents a divalent hydrocarbon group which forms a divalent alicyclic hydrocarbon group together with the adjacent carbon atom connected to R. Examples of the divalent alicyclic hydrocarbon group formed by the divalent hydrocarbon group with the adjacent carbon atom include a cyclopropan-1,1-diyl group, a cyclobutan-1,1-diyl group, a cyclopentane-1,1-diyl group, a cyclohexane-1,1-diyl group, a norbornan-2,2-diyl group, an adamantan-2,2-diyl, and the like.

Specific examples of the structural unit of the formula (I) include the followings:

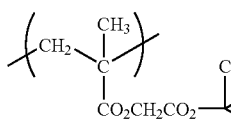 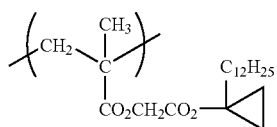
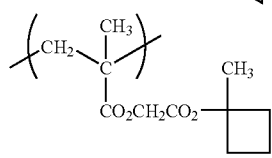 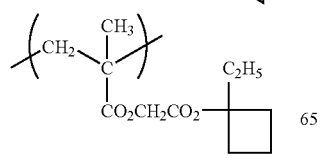

-continued

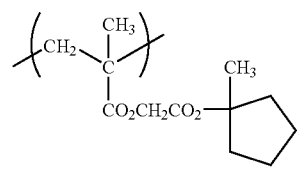
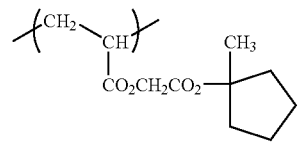
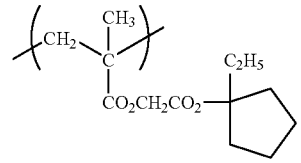
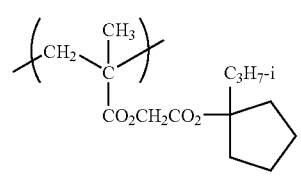
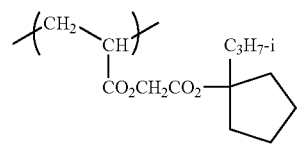
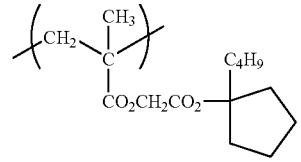
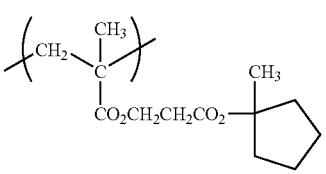
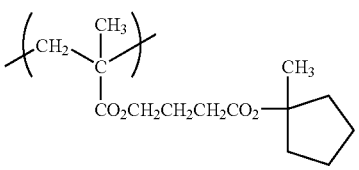
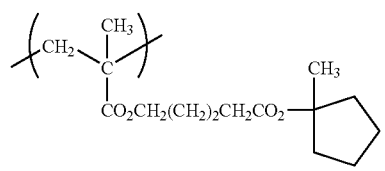
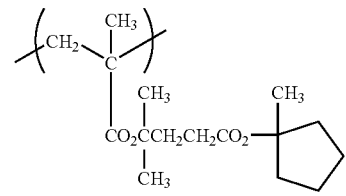

-continued
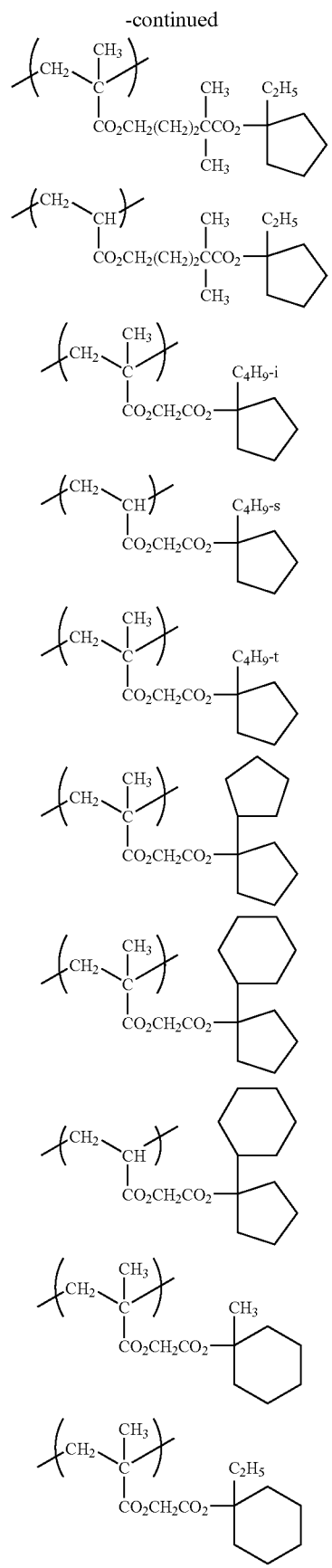
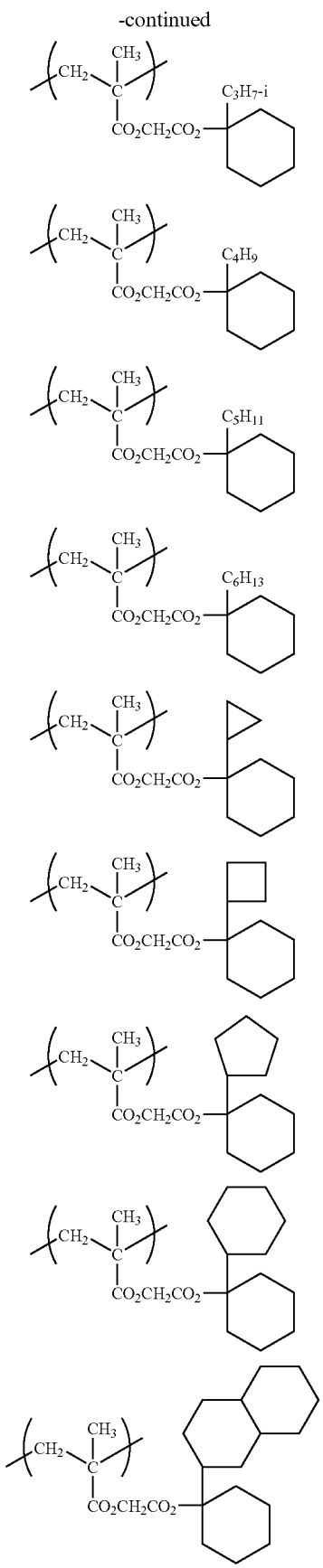

-continued
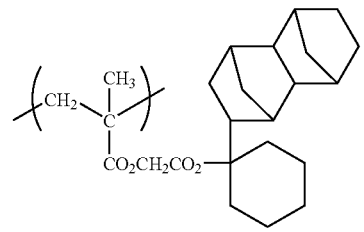
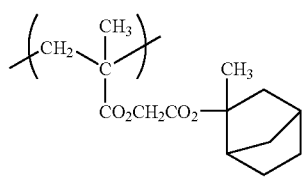
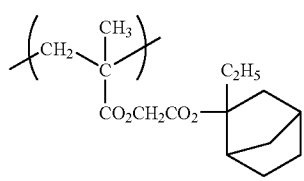
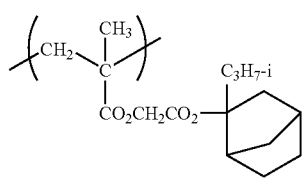
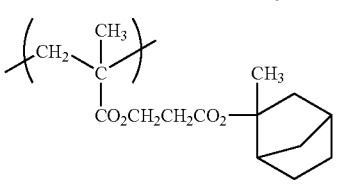
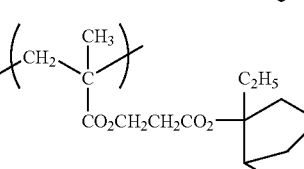
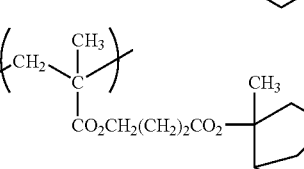
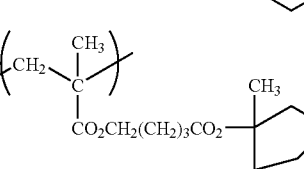
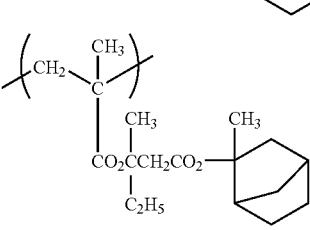
-continued
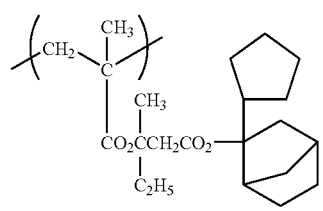
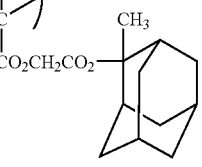
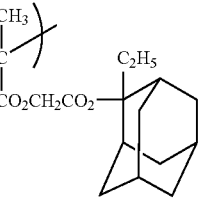
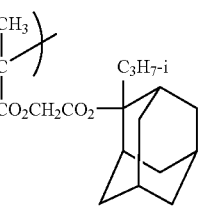
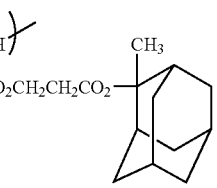
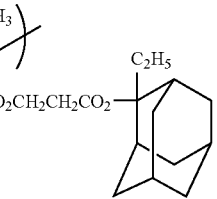
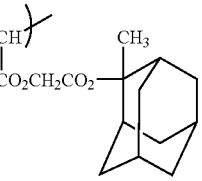
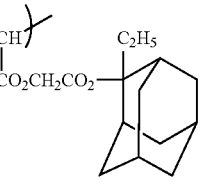

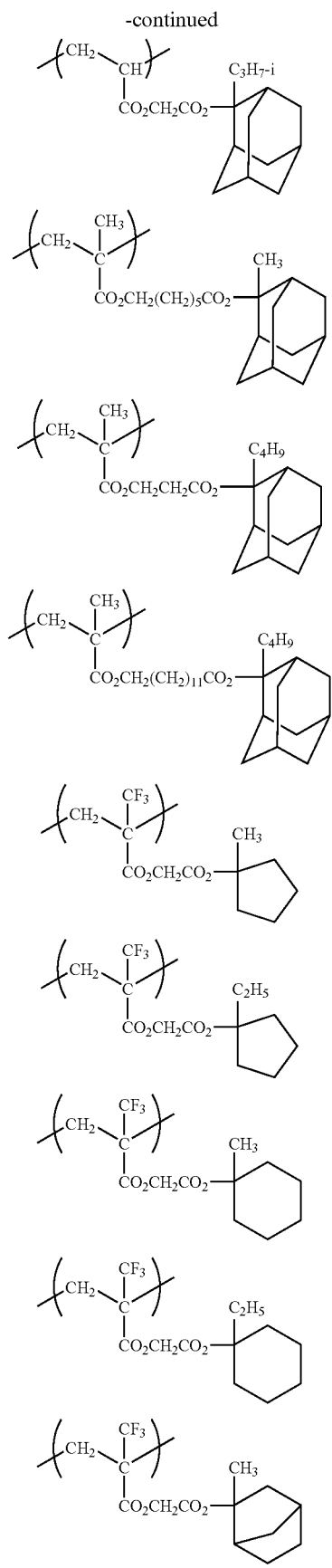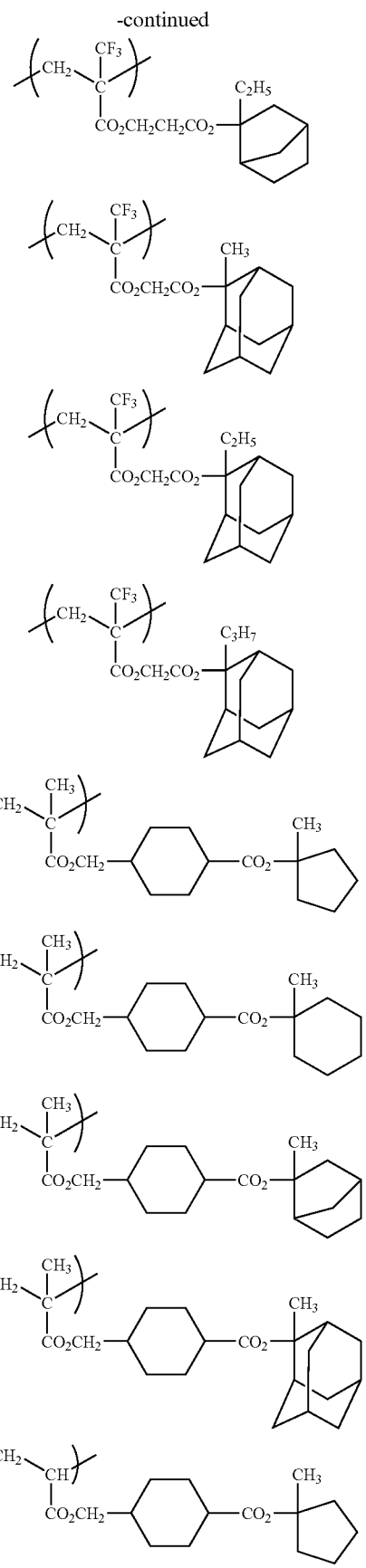

-continued

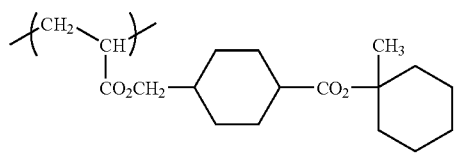

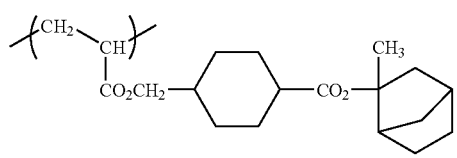

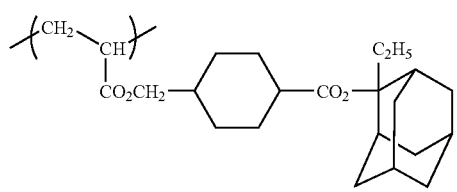

As described later in the production method of RESIN in detail, the structural unit of the formula (I) can be formed by polymerizing a (meth)acrylic derivative of the formula (XXII)

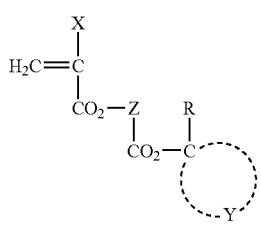

(XXII)

wherein X, Y, Z and R have the same meanings as defined above.

The (meth)acrylic derivative of the formula (XXII) can be obtained by reacting an alcohol derivative of the formula (XXIII) with an acid halide derivative of the formula (XXIV) to obtain a condensate, and reacting the condensate with an carboxylic acid of the formula (XXIV') according to the following equation. In the equation, $W^1$ and $W^2$ each independently represents a chlorine atom, a bromine atom or an iodine atom and X, Y, Z and R have the same meanings as defined above.

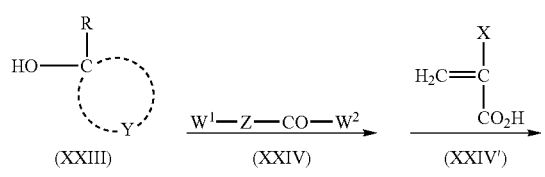

-continued

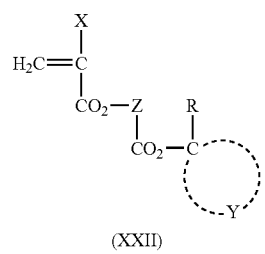

(XXII)

Examples of the alcohol derivatives of the formula (XXIII) include the following compounds:

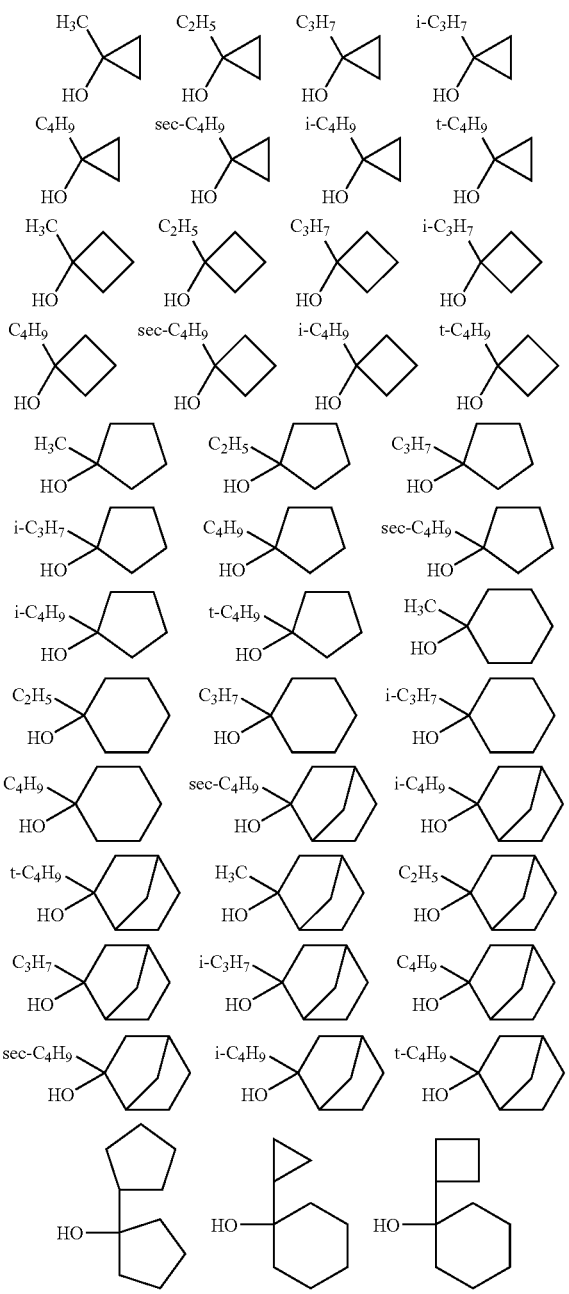

-continued

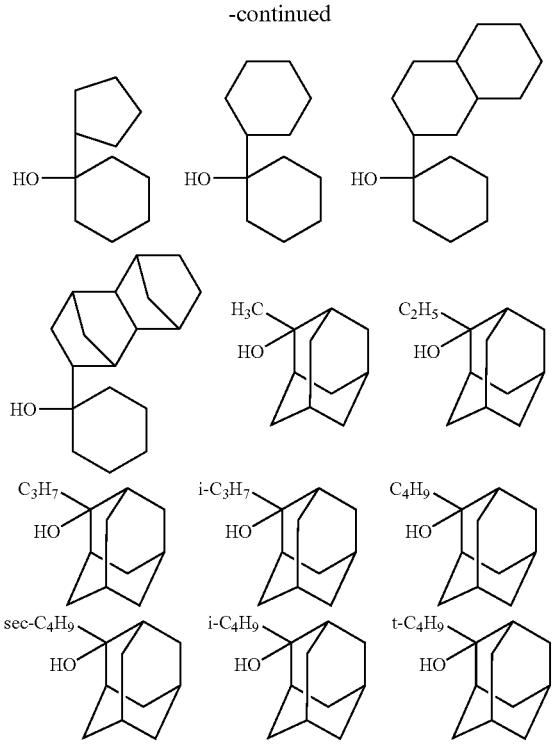

Examples of the acid halide derivatives of the formula (XXIV) include the following compounds.

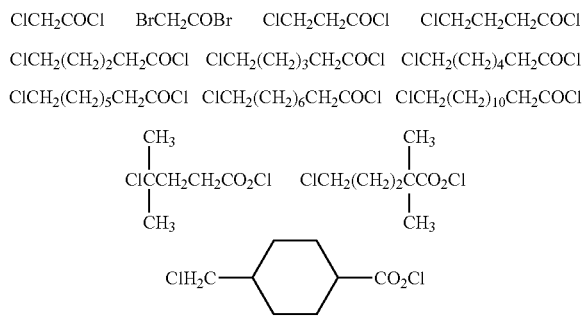

Examples of the carboxylic acid of the formula (XXIV') include an acrylic acid, a methacrylic acid, an α-trifluoromethylmethacrylic acid, and the like.

The reaction between the alcohol derivative of the formula (XXIII) and the acid halide derivative of the formula (XXIV) is conducted in, for example, an inert solvent such as toluene, tetrahydrofuran, dimethylformamide, dimethylsulfoxide, and the like. The reaction temperature is usually −30 to +200° C., preferably 0 to 100° C. The reaction is preferably conducted in the presence of deacidifying agent. Examples thereof include organic basic compounds such as triethylamine, pyridine, and the like, inorganic basic compounds such as potassium carbonate, sodium hydroxide, and the like, and a mixture of at least two kind thereof can also be used.

The amount of the acid halide derivative of the formula (XXIV) is usually 1 to 2 gram equivalent, preferably 1 to 1.5 gram equivalent per one mol of the alcohol derivative of the formula (XXIII). The amount of the deacidifying agent is usually 1 to 5 gram equivalent, preferably 1 to 3 gram equivalent per one mol of the alcohol derivative of the formula (XXIII). The reaction can also be conducted by adding phase transfer catalysts such as tetrabutylammonium bromide, and the like.

The condensate obtained can be taken out according to the conventional after-treatment and can be purified, for example, by chromatography, recrystallization, distillation, or the like.

The (meth)acrylic derivative of the formula (XXII) can be produced by reacting the condensate above, which has the formula,

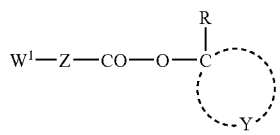

with the carboxylic acid of the formula (XXIV') in the presence of a deacidifying agent.

The reaction is usually conducted in an inert solvent such as toluene, tetrahydrofuran, dimethylformamide, dimethylsulfoxide, and the like. The reaction temperature is usually −30 to +200° C., preferably 0 to 100° C.

Examples of the deacidifying agents include organic basic compounds such as triethylamine, pyridine, and the like, inorganic basic compounds such as potassium carbonate, sodium hydroxide, and the like, and a mixture of at least two kind thereof can also be used.

The amount of the carboxylic acid of the formula (XXIV') is usually 1 to 2 gram equivalent, preferably 1 to 1.5 gram equivalent per one mol of the condensate. The amount of the deacidifying agent is usually 1 to 5 gram equivalent, preferably 1 to 3 gram equivalent per one mol of the condensate. The reaction can also be conducted by adding phase transfer catalysts such as tetrabutylammonium bromide, and the like.

The (meth)acrylic derivative of the formula (XXII) obtained can be taken out according to the conventional after-treatment and can be purified, for example, by chromatography, recrystallization, distillation, or the like.

In the structural unit of the formula (II), $X^1$ represents a hydrogen atom, an alkyl group having 1 to 4 carbon atoms such as a methyl group, an ethyl group, and the like, or a perfluoroalkyl group having 1 to 4 carbon atoms such as a trifluoromethyl group, a pentafluoroethyl group. $Z^1$ represents a divalent hydrocarbon group having 1 to 12 carbon atoms, and examples thereof include alkylene groups such as a methylene group, ethylidene group, a propylidene group, and the like; polymethylene groups such as an ethylene group, a propylene group, a 1,2-butylene group, a trimethylene group, a tetramethylene group, a pentamethylene group, a hexamethylene group, a heptamethylene group, an octamethylene group, a dodecamethylene group, 1,1-dimethyltrimethylene group, a 1,1-dimethyltetramethylene group, and the like; groups shown by -Pm-Cy- such as

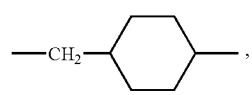

and the like, wherein Pm represents an optionally substituted (poly)methylene group having 1 to 4 carbon atoms and Cy represents a cycloalkan-diyl group having 3 to 8 carbon atoms. $n^1$ represents an integer of 0 to 3. $R^1$ represents an alkyl group having 1 to 6 carbon atoms such as a methyl group, an ethyl group, an isopropyl group, a n-butyl group, an isobutyl group, a sec-butyl group, a tert-butyl group, and the like; or an alicyclic hydrocarbon group having 3 to 12 carbon atoms such as a cyclopropyl group, a cyclobutyl group, a cyclopentyl group, a cyclohexyl group, a decahydronaphthyl group, a decahydro-1,4:5,8-dimethanonaphthyl group, and the like. Y has the same meaning as defined above. However, the structural unit of the formula (II) is different from the structural unit of the formula (I). It is usual that $n^1$ is not 1.

Specific examples of the structural unit of the formula (II) include the followings:

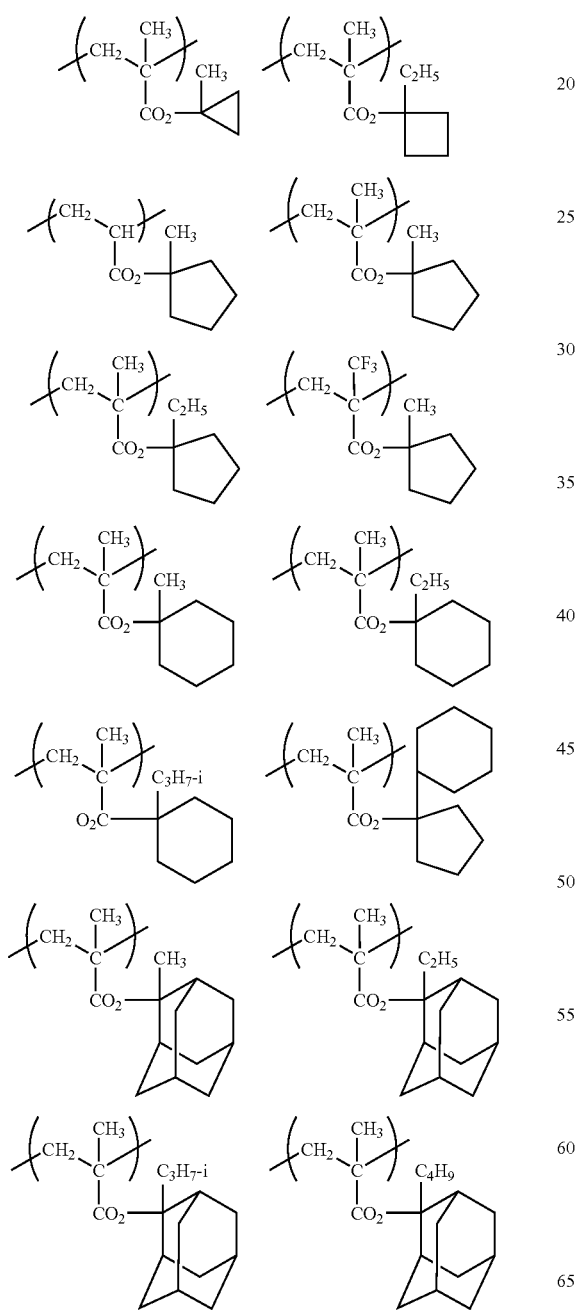
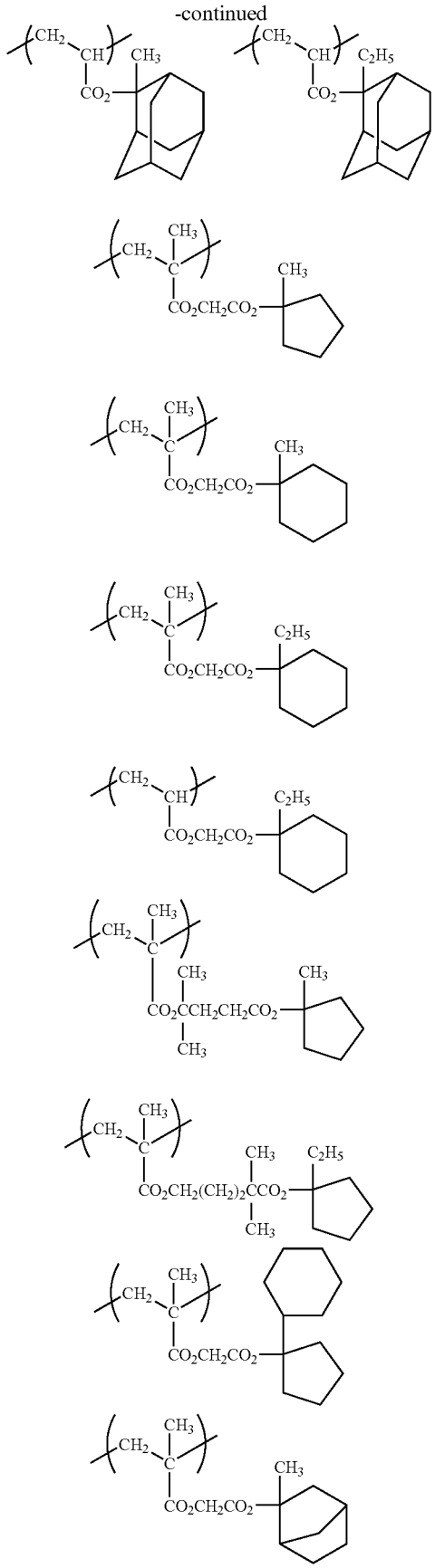

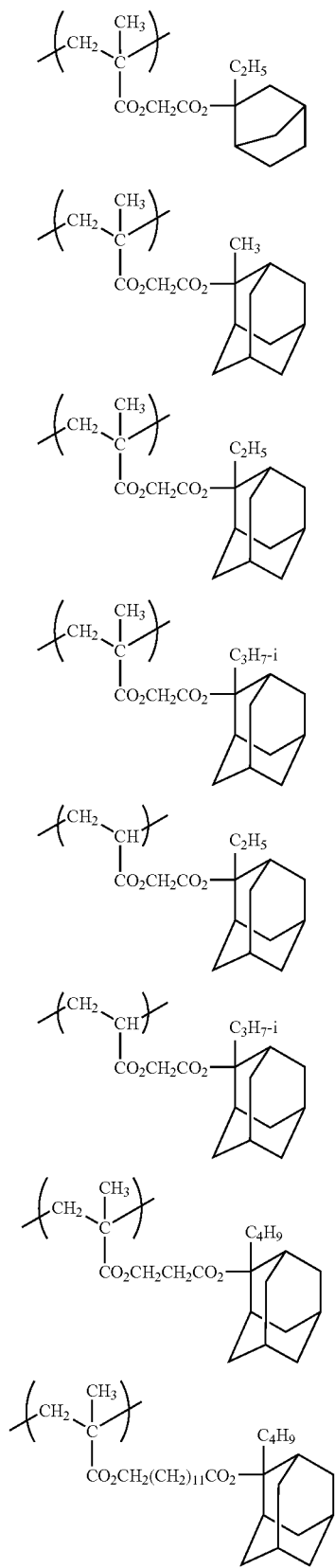
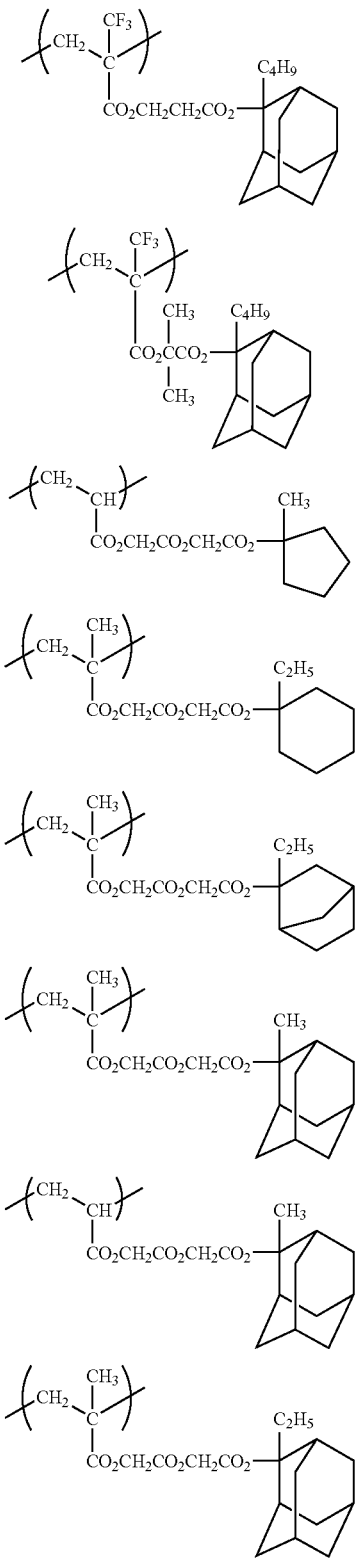
As described later in the production method of RESIN in detail, the structural unit of the formula (II) can be formed by polymerizing a (meth)acrylic derivative of the formula (II')

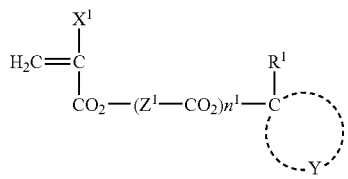

wherein $X^1$, $R^1$, Y, $Z^1$ and $n^1$ have the same meanings as defined above.

The (meth)acrylic derivative of the formula (II') can be produced in the same manner as in the synthetic method of the (meth)acrylic derivative of the formula (XXII) above.

In the structural unit of the formula (III), $X^2$ represents a hydrogen atom, an alkyl group having 1 to 4 carbon atoms such as a methyl group, an ethyl group, and the like, or a perfluoroalkyl group having 1 to 4 carbon atoms such as a trifluoromethyl group, a pentafluoroethyl group. $Z^2$ represents a divalent hydrocarbon group having 1 to 12 carbon atoms, and examples thereof include alkylene groups such as a methylene group, ethylidene group, a propylidene group, and the like; polymethylene groups such as an ethylene group, a propylene group, a 1,2-butylene group, a trimethylene group, a tetramethylene group, a pentamethylene group, a hexamethylene group, a heptamethylene group, an octamethylene group, a dodecamethylene group, 1,1-dimethyltrimethylene group, a 1,1-dimethyltetramethylene group, and the like; groups shown by -Pm-Cy- such as

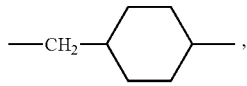

and the like, wherein Pm represents an optionally substituted (poly)methylene group having 1 to 4 carbon atoms and Cy represents a cycloalkan-diyl group having 3 to 8 carbon atoms. $n^2$ represents an integer of 0 to 3. A represents a hydrocarbon group having 1 to 12 carbon atoms, examples thereof include alkyl such as a methyl group, an ethyl group, a isopropyl group, n-propyl group, n-butyl group, an isobutyl group, a sec-butyl group, a tert-butyl group, and the like, an alicyclic hydrocarbon group having 3 to 12 carbon atoms such as a cyclopropyl group, a cyclobutyl group, a cyclopentyl group, a cyclohexyl group, a decahydronaphthyl group, a decahydro-1,4:5,8-dimethanonaphthyl group, and the like. Y has the same meaning as defined above. However, the structural unit of the formula (III) is different from the structural unit of the formula (I). It is usual that $n^2$ is not 1.

Specific examples of the structural unit of the formula (III) include the followings:

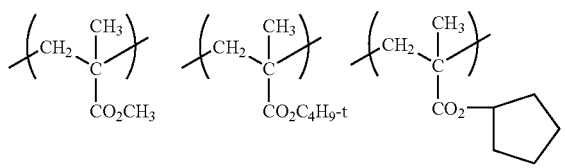

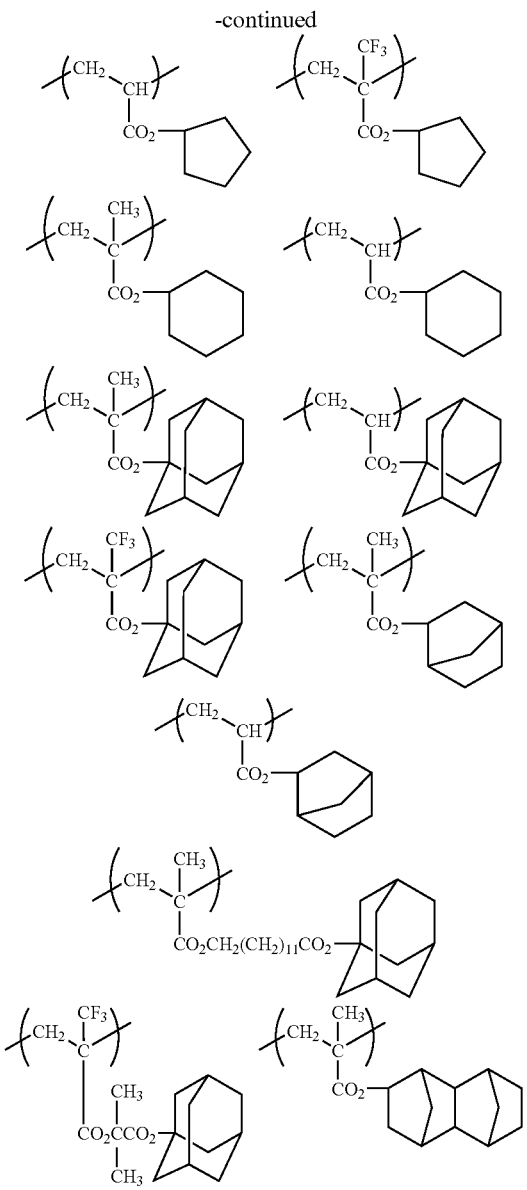

As described later in the production method of RESIN in detail, the structural unit of the formula (III) can be formed by polymerizing a (meth)acrylic derivative of the formula (III')

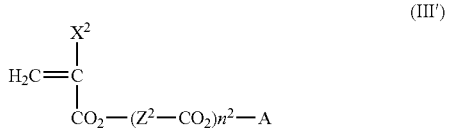

wherein $X^2$, $Z^2$, A and $n^2$ have the same meanings as defined above.

The (meth)acrylic derivative of the formula (III') can be produced in the same manner as in the synthetic method of the (meth)acrylic derivative of the formula (XXII) above.

In the structural unit of the formula (IV), $X^3$ represents a hydrogen atom, an alkyl group having 1 to 4 carbon atoms such as a methyl group, an ethyl group, and the like, or a perfluoroalkyl group having 1 to 4 carbon atoms such as a trifluoromethyl group, a pentafluoroethyl group. $Z^3$ represents a divalent hydrocarbon group having 1 to 12 carbon atoms, and examples thereof include alkylene groups such as a methylene group, ethylidene group, a propylidene group, and the like; polymethylene groups such as an ethylene group, a propylene group, a 1,2-butylene group, a trimethylene group, a tetramethylene group, a pentamethylene group, a hexamethylene group, a heptamethylene group, an octamethylene group, a dodecamethylene group, 1,1-dimethyltrimethylene group, a 1,1-dimethyltetramethylene group, and the like; groups shown by -Pm-Cy- such as

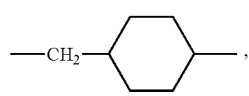

and the like, wherein Pm represents an optionally substituted (poly)methylene group having 1 to 4 carbon atoms and Cy represents a cycloalkan-diyl group having 3 to 8 carbon atoms. $n^3$ represents an integer of 0 to 3. $R^2$ and $R^3$ each independently represents a hydroxyl group or a hydroxymethyl group. p represents an integer of 0 to 2.

Specific examples of the structural unit of the formula (IV) include the followings:

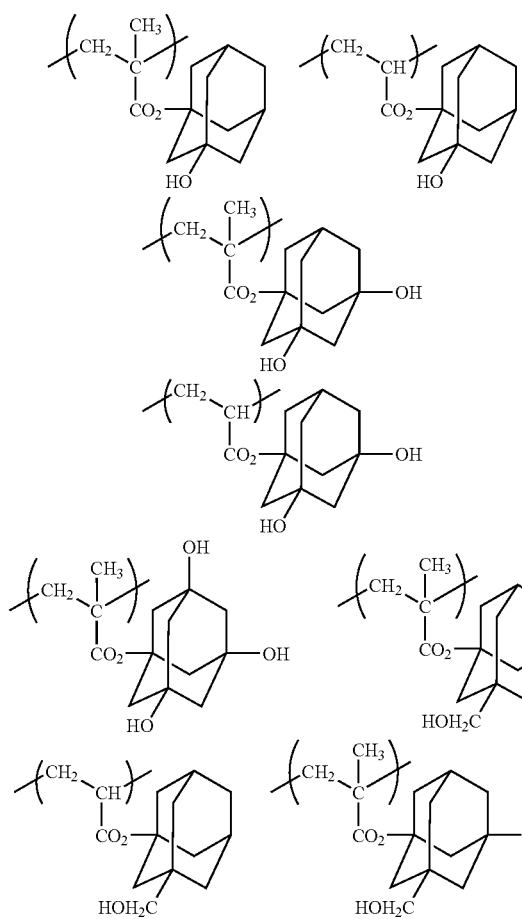

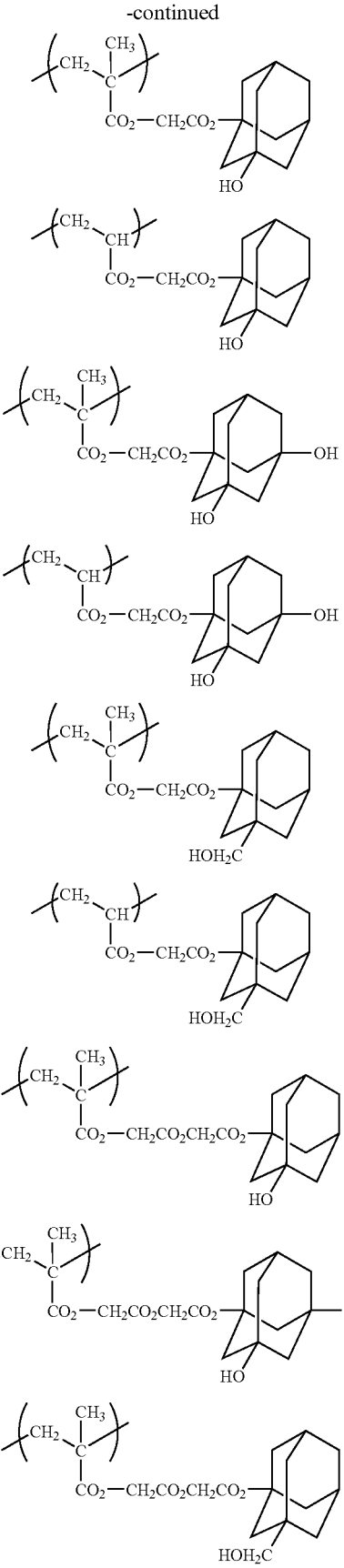

-continued

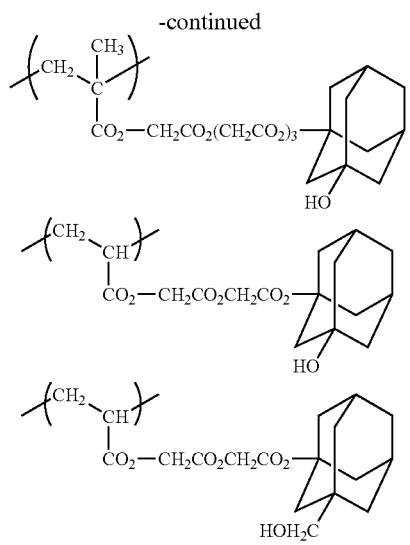

As described later in the production method of RESIN in detail, the structural unit of the formula (IV) can be formed by polymerizing a (meth)acrylic derivative of the formula (XXV)

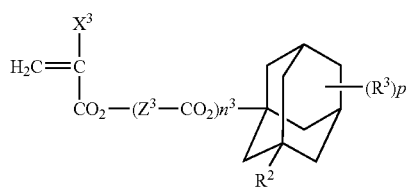
(XXV)

wherein $X^3$, $R^2$, $R^3$, $Z^3$, $n^3$ and p have the same meanings as defined above.

The (meth)acrylic derivative of the formula (XXV) can be obtained by reacting an alcohol derivative of the formula (XXVII)

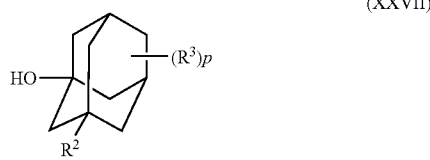
(XXVII)

wherein $R^2$, $R^3$ and p have the same meanings as defined above, with a carboxylic acid derivative of the formula (XXVI)

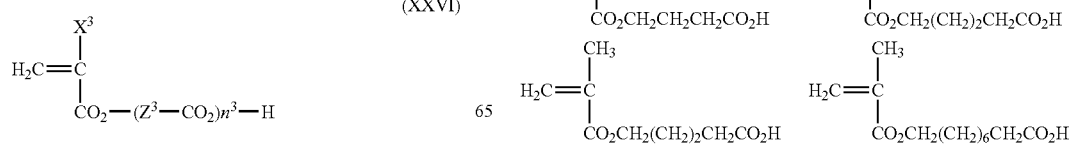
(XXVI)

wherein $X^3$, $Z^3$ and $n^3$ have the same meanings as defined above, preferably in the presence of an acidic catalyst according to the following equation.

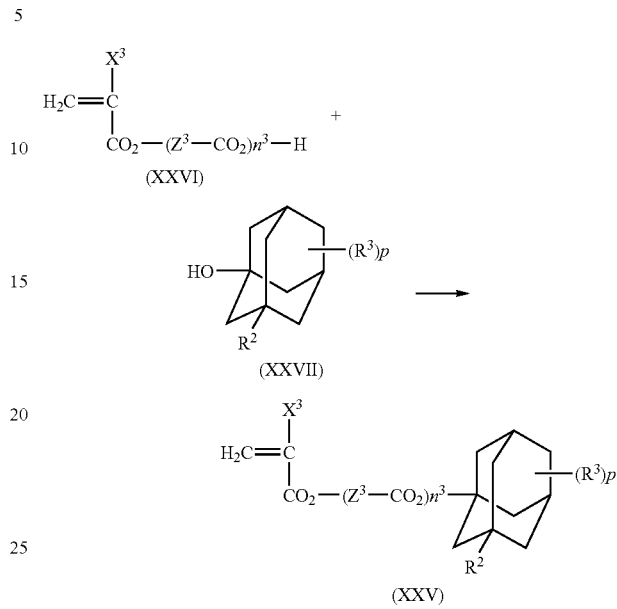

Examples of the alcohol derivatives of the formula (XXVII) include the following compounds:

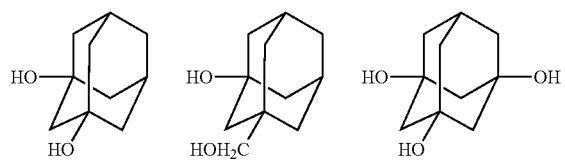

Examples of the carboxylic acid derivatives of the formula (XXVI) include the following compounds:

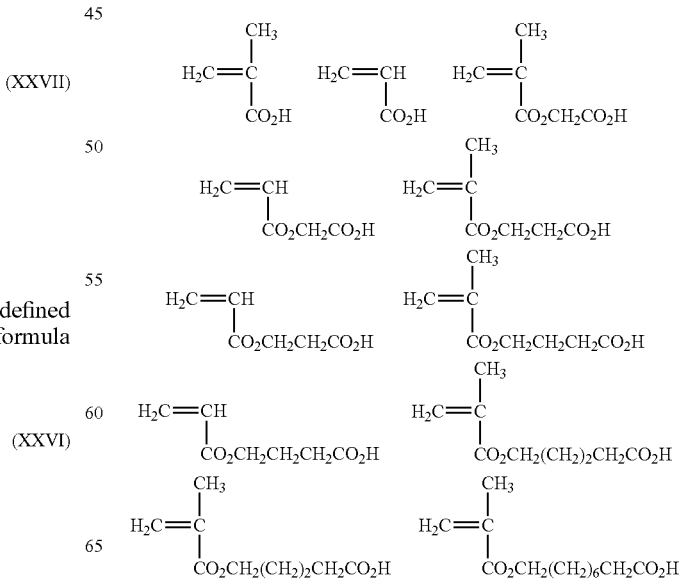

-continued $H_2C=CH$
$|$
$CO_2CH_2(CH_2)_6CH_2CO_2H$ $H_2C=C(CH_3)$
$|$
$CO_2CH_2(CH_2)_{10}CH_2CO_2H$ $H_2C=CH$
$|$
$CO_2CH_2(CH_2)_{10}CH_2CO_2H$ $H_2C=C(CH_3)$
$|$
$CO_2CH_2CO_2CH_2CO_2H$ $H_2C=CH$
$|$
$CO_2CH_2CO_2CH_2CO_2H$ $H_2C=C(CH_3)$
$|$
$CO_2CH_2CO_2CH_2CO_2CH_2CO_2H$ $H_2C=C(CH_3)$
$|$
$CO_2CH_2CO_2CH_2CO_2CH_2CO_2H$ $H_2C=C(CH_3)$  $CH_3$
$|$            $|$
$CO_2C\!-\!CO_2H$
$|$
$CH_3$ $H_2C=CH$  $CH_3$
$|$        $|$
$CO_2C\!-\!CO_2H$
$|$
$CH_3$ $H_2C=C(CH_3)$  $CH_3$
$|$             $|$
$CO_2CH_2CO_2CCO_2H$
$|$
$CH_3$ $H_2C=CH$  $CH_3$
$|$        $|$
$CO_2CH_2CO_2CCO_2H$
$|$
$CH_3$ $H_2C=C(CF_3)$
$|$
$CO_2H$ $H_2C=C(CF_3)$
$|$
$CO_2CH_2CO_2H$ $H_2C=C(C_2F_5)$
$|$
$CO_2H$ $H_2C=C(C_3F_7)$
$|$
$CO_2H$ $H_2C=C(C_4F_9)$
$|$
$CO_2H$ The reaction is an esterification reaction by dehydration of the alcohol derivative of the formula (XXVII) and the carboxylic acid derivative of the formula (XXVI), and is usually conducted in an inert solvent such as toluene, dichloroethane, tetrahydrofuran, dimethylformamide, dimethylsulfoxide, and the like. The reaction temperature is usually −30 to +200° C., preferably 0 to 150° C.

When the reaction is conducted by co-distillation dehydration, an acidic catalyst is preferably added. Examples thereof include organic acids such as p-toluenesulfonic acid, trifluoroacetic acid, trifluoromethanesulfonic acid, and the like, acidic catalyst resin such as perfluorinated ion-exchange resin (e.g. Nafion®), and a mixture of at least two kind thereof can also be used. Or alternatively, the (meth)acrylic acid derivative of the formula (XXVI) can be used as a acidic catalyst, as a reactant, and as a solvent.

The amount of the (meth)acrylic acid derivative of the formula (XXVI) agent is usually 1 mol or more, preferably 1 to 1.5 mol per one mol of the alcohol derivative of the formula (XXVII). The amount of the acidic catalyst is usually catalytic amount to one mol, preferably catalytic amount to 0.5 mol per one mol of the alcohol derivative of the formula (XXVII). In the esterification reaction by dehydration, dehydrating agents such as dicyclohexylcarbodiimide can be used instead of the acidic catalysts. When secondary hydroxyl group coexists with primary hydroxyl group, the primary hydroxyl group is preferably inactivated by protecting group such as silyl group.

The (meth)acrylic derivative of the formula (XXV) obtained can be taken out according to the conventional after-treatment and can be purified, for example, by chromatography, recrystallization, distillation, or the like.

In the structural unit of the formula (V), $X^4$ represents a hydrogen atom, an alkyl group having 1 to 4 carbon atoms such as a methyl group, an ethyl group, and the like, or a perfluoroalkyl group having 1 to 4 carbon atoms such as a trifluoromethyl group, a pentafluoroethyl group. $Z^4$ represents a divalent hydrocarbon group having 1 to 12 carbon atoms, and examples thereof include alkylene groups such as a methylene group, ethylidene group, a propylidene group, and the like; polymethylene groups such as an ethylene group, a propylene group, a 1,2-butylene group, a trimethylene group, a tetramethylene group, a pentamethylene group, a hexamethylene group, a heptamethylene group, an octamethylene group, a dodecamethylene group, 1,1-dimethyltrimethylene group, a 1,1-dimethyltetramethylene group, and the like; groups shown by -Pm-Cy- such as

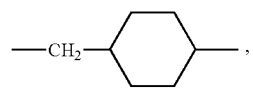

and the like, wherein Pm represents an optionally substituted (poly)methylene group having 1 to 4 carbon atoms and Cy represents a cycloalkan-diyl group having 3 to 8 carbon atoms. $n^4$ represents an integer of 0 to 3. G represents —(CO)O— or —O—. $R^4$ represents an alkyl group having 1 to 4 carbon atoms such as a methyl group, an ethyl group, a n-propyl group, an isopropyl group, a n-butyl group, an isobutyl group, a sec-butyl group, a tert-butyl group or an alkoxy group having 1 to 4 carbon atoms such as a methoxy group, an ethoxy group, a n-propoxy group, an isopropyl group, a n-butoxy group, an isobutoxy group, a sec-butoxy group, a tert-butoxy group, and the like. q represents an integer of 0 to 2.

Specific examples of the structural unit of the formula (V) include the followings:

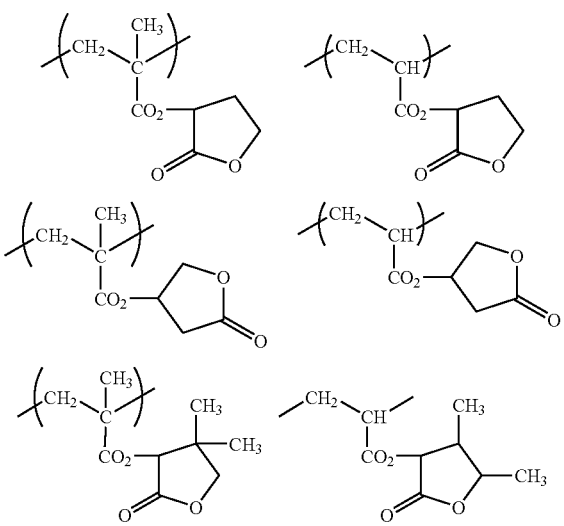

-continued
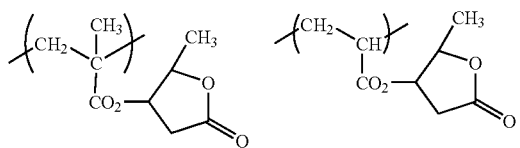
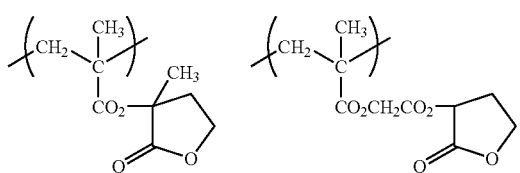
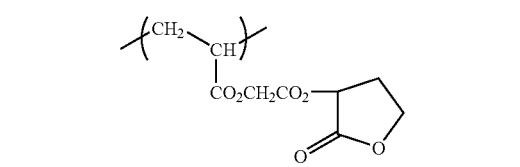
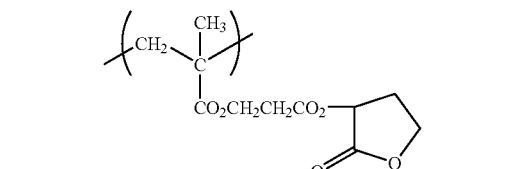
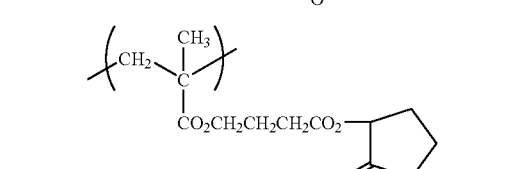
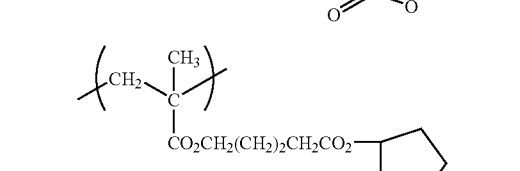
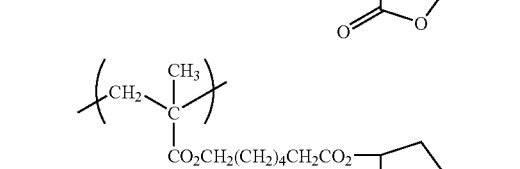
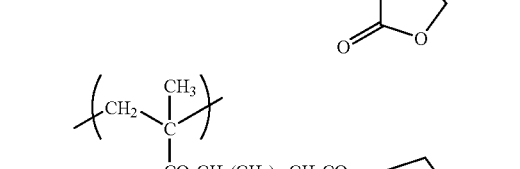
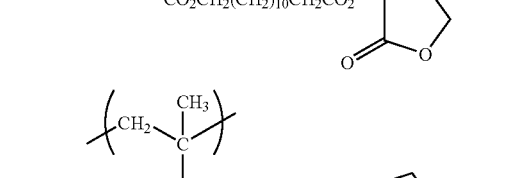
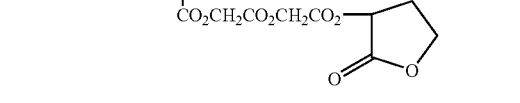
-continued
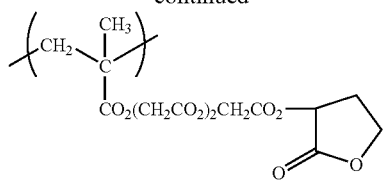

-continued

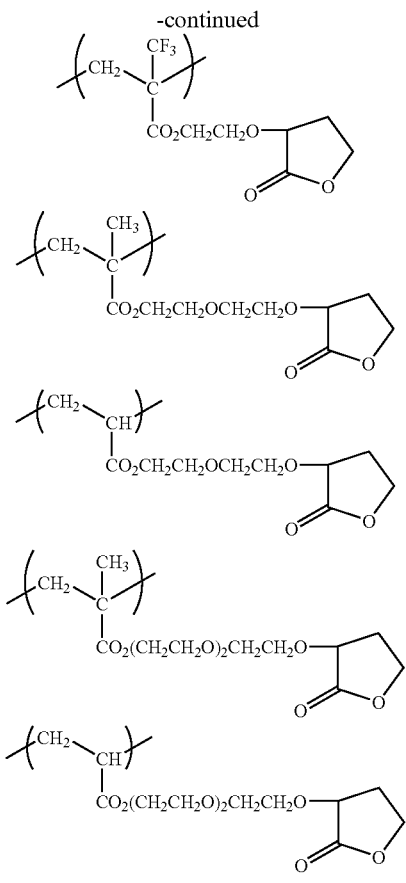

As described later in the production method of RESIN in detail, the structural unit of the formula (V) can be formed by polymerizing a (meth)acrylic derivative of the formula (XXVIII)

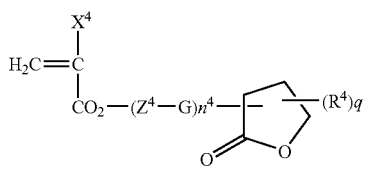

(XXVIII)

wherein $X^4$, $R^4$, $Z^4$, G, $n^4$ and q have the same meanings as defined above.

The (meth)acrylic derivative of the formula (XXVIII) can be obtained by reacting a γ-butyrolactone derivative of the formula (XXX)

(XXX)

wherein $W^3$ represents a chlorine atom, and $R^4$ and q have the same meanings as defined above,
with an alcohol derivative of the formula (XXIX) in the presence of a basic compound,

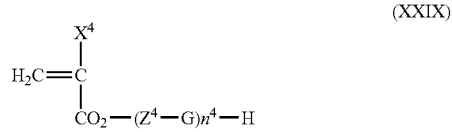

(XXIX)

wherein $X^4$, $Z^4$, G and $n^4$ have the same meanings as defined above, according to the following equation.

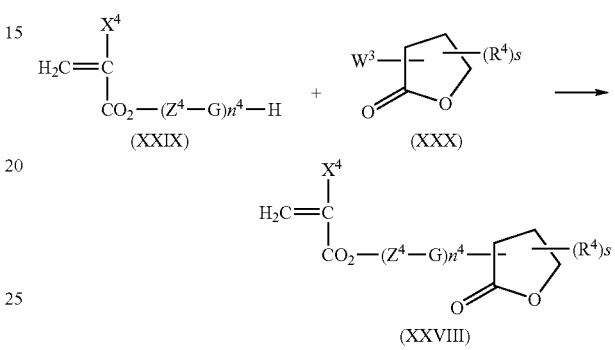

Examples of the alcohol derivatives of the formula (XXIX) include the following compounds:

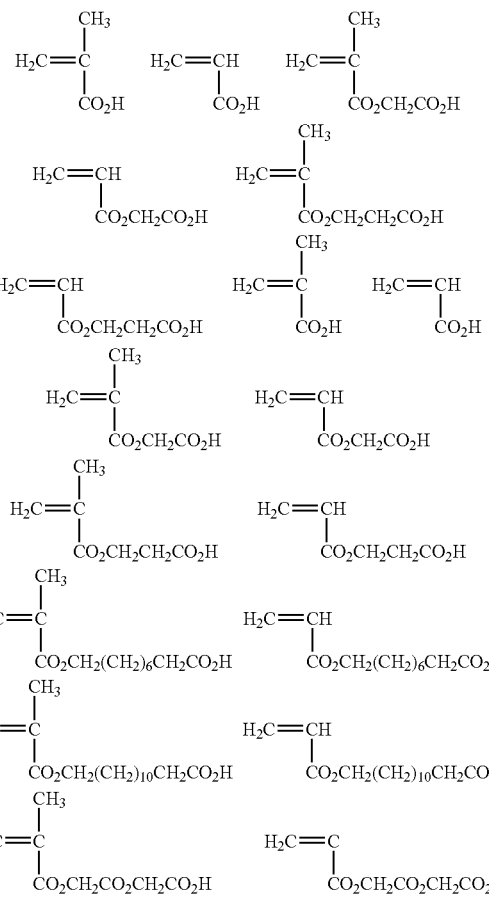

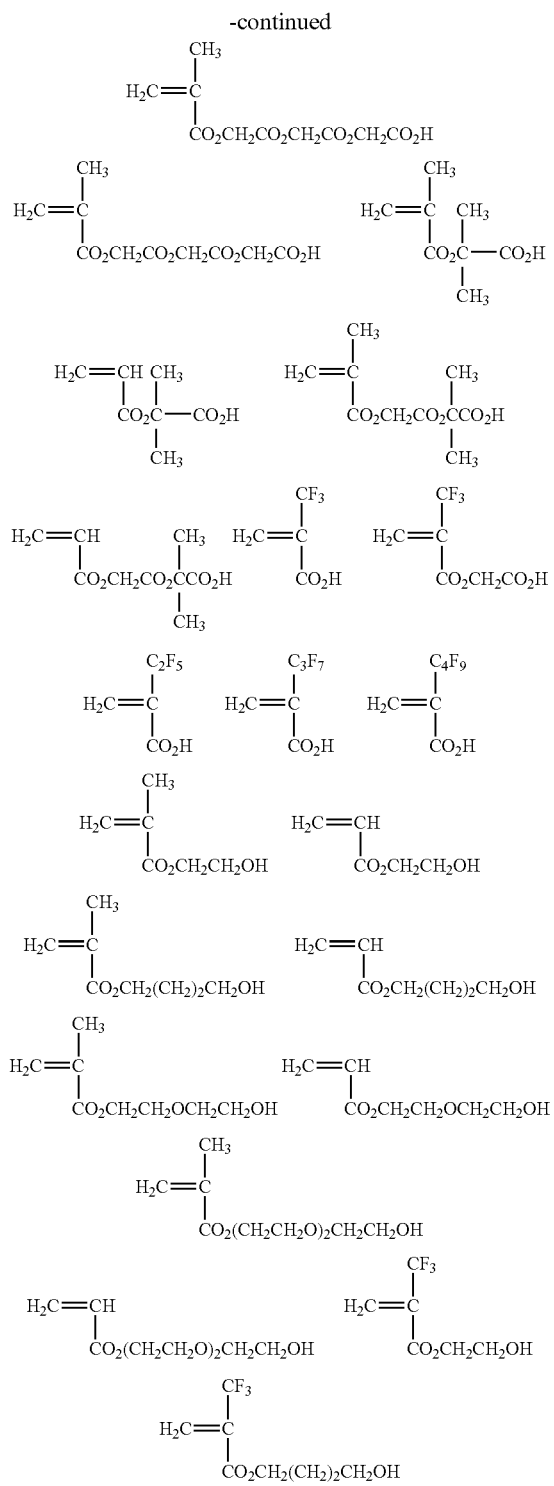

Examples of the γ-butyrolactone derivatives of the formula (XXX) include the following compounds:

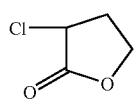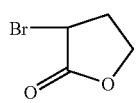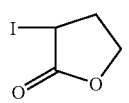

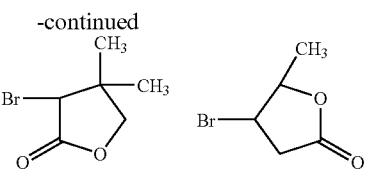

The reaction between γ-butyrolactone derivative of the formula (XXX) and the alcohol derivative of the formula (XXIX) is usually conducted in an inert solvent such as toluene, tetrahydrofuran, dimethylformamide, dimethylsulfoxide, and the like. The reaction temperature is usually −30 to +200° C., preferably 0 to 150° C.

It is preferable that a deacidifying agent is added in the reaction. Examples thereof include organic basic compounds such as triethylamine, pyridine, and the like, inorganic basic compounds such as potassium carbonate, sodium hydroxide, and the like, and a mixture of at least two kind thereof can also be used.

The amount of the hydroxy derivative of the formula (XXIX) is usually 1 to 2 mol equivalent, preferably 1 to 1.5 mol equivalent per one mol of the g-lactone derivative of the formula (XXX). The amount of the deacidifying agent is usually 1 to 5 mol equivalent, preferably 1 to 3 mol equivalent per one mol of the condensate. The reaction can also be conducted by adding phase transfer catalysts such as tetrabutylammonium bromide, and the like.

The (meth)acrylic derivative of the formula (XXVIII) obtained can be taken out according to the conventional after-treatment and can be purified, for example, by chromatography, recrystallization, distillation, or the like.

RESIN can be produced by polymerizing (meth)acrylic derivative of the formula (XXII) and at least one monomer selected from the group consisting of (meth)acrylic derivatives of the formulas (II'), (III'), (XXV) and (XXVIII). Optionally, other monomer(s), such as a monomer which leads to a structural unit having acid-labile group derived from known (meth)acrylate(s), and a monomer which leads to a structural unit not dissociated or not easily dissociated by the action of an acid, as long as the effect of the present invention is not prevented.

Examples of methods for producing RESIN include radical polymerization method, anion polymerization method, coordination polymerization method, and the like, and radical polymerization method is preferred.

As polymerization initiators used therein, the ones effectively generating radicals by heating are preferred. Examples thereof include azo compounds such as 2,2'-azobisisobutyronitrile, dimethyl 2,2'-azobisisobutylate, 2,2'-azobis(2,4-dimethylvaleronitrile), 2,2'-azobis(2-methylbutyronitrile), and the like; organic peroxides such as 2,5-dimethyl-2,5-bis(tert-butylperoxy)hexane, tert-hexyl peroxypivalate, and the like. Each of the polymerization initiator can be used alone or in combination with at least one other kind.

Chain transfer agents such as 1-butanethiol, 2-butanethiol, 1-octanethiol, 1-decanethiol, 1-tetradecanethiol, cyclohexanethiol, 2-methyl-1-propanethiol, and the like, can also be used.

Preferred organic solvents used for the production of RESIN are the ones capable of dissolving all of monomers, polymerization initiators and copolymer obtained. Examples thereof include hydrocarbons such as toluene, and the like, 1,4-dioxane, tetrahydrofuran, methyl isobutyl ketone, isopropyl alcohol, γ-butyrolactone, propylene glycol monomethyl ether acetate, ethyl lactate, and the like. Each of the solvent can be used alone or in combination with at least one other kind.

The polymerization temperature is usually 0 to 150° C., preferably 40 to 100° C.

The weight average molecular weight of RESIN is preferably 1000 to 500000, and more preferably 4000 to 50000.

RESIN contains usually 1 to 80% by mol, preferably 5 to 60% by mol of the structural unit of the formula (I), and usually 20 to 99% by mol, preferably 40 to 95% by mol of at least one monomer selected from the group consisting of the structural units of the formulas (II), (III), (IV) and (V), all based on total of structural units in RESIN. Total content of the structural units of the formulas (I), (II), (III), (IV) and (V) is generally 70 to 100% by mol, preferably 90 to 100% by mol.

The ratio of each of the structural units can generally be determined by conventional method, for example, by NMR analysis.

For the present composition, RESIN preferably comprises a structural unit of the formula (VI)

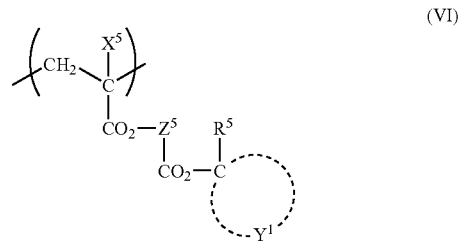
(VI)

wherein $X^5$ represents a hydrogen atom, an alkyl group having 1 to 4 carbon atoms or a perfluoroalkyl group having 1 to 4 carbon atoms, $Y^1$ represents at least two atoms necessary to form an alicyclic hydrocarbon group having 2 to 12 carbon atoms together with the adjacent carbon atom, $Z^5$ represents a divalent hydrocarbon group, $R^5$ represents an alkyl group having 1 to 6 carbon atoms or an alicyclic hydrocarbon group having 3 to 12 carbon atoms, and at least one structural unit selected from the group consisting of the structural units of the formulas (III), (VII) and (VIII)

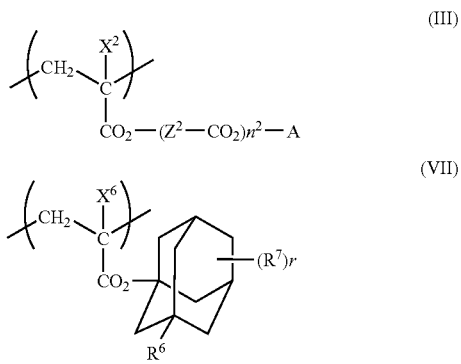
(III)

(VII)

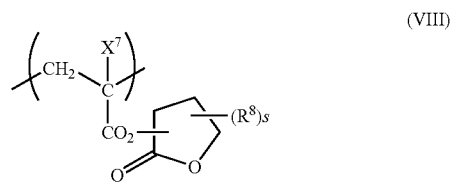
(VIII)

wherein $X^6$ and $X^7$ each independently represents a hydrogen atom, an alkyl group having 1 to 4 carbon atoms or a perfluoroalkyl group having 1 to 4 carbon atoms, $R^6$ and $R^7$ each independently represents a hydroxy group or a hydroxymethyl group, $R^4$ represents an alkyl group having 1 to 4 carbon atoms or an alkoxy group having 1 to 4 carbon atoms, r and s each independently represents an integer of 0 to 2.

For the present composition, RESIN more preferably comprises a structural unit of the formula (IX)

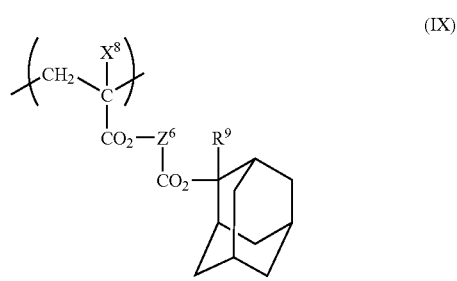
(IX)

wherein $X^8$ represents a hydrogen atom, an alkyl group having 1 to 4 carbon atoms or a perfluoroalkyl group having 1 to 4 carbon atoms, $Z^6$ represents a methylene group, an ethylene group, a trimethylene group or a tetramethylene group, and $R^9$ represents an alkyl group having 1 to 4 carbon atoms, and at least one structural unit selected from the group consisting of the structural units of the formulas (VII) and (VIII).

For the present composition, it is particularly preferable that RESIN comprises a structural unit of the formula (X)

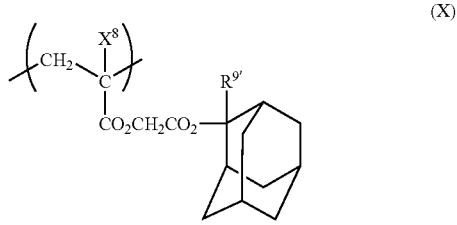
(X)

wherein $X^8$ represents a hydrogen atom or a methyl group, and $R^{9'}$ represents a methyl group, an ethyl group, isopropyl group or a butyl group, and at least one structural unit selected from the group consisting of structural units of the formulas (XI) and (VIII')

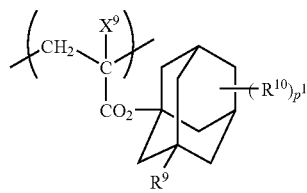 (XI)

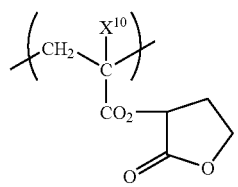 (VIII')

wherein $X^9$ and $X^{10}$ each independently represents a hydrogen atom, an alkyl group having 1 to 4 carbon atoms or a perfluoroalkyl group having 1 to 4 carbon atoms, $R^9$ and $R^{10}$ each independently represents a hydroxy group or a hydroxymethyl group, and $p^1$ represents 0 or 1.

The acid generator, another component of the present composition, is the compound which is decomposed to generate an acid by allowing radioactive ray such as light and electron beam to act on the acid generator itself or a resist composition containing the acid generator. The acid generated from the acid generator acts on RESIN, to dissociate acid-labile group present in RESIN.

Such acid generators include, for example, onium salt, organic halogen compounds, sulfone compounds, sulfonate compounds, and the like.

Specific examples thereof include the followings:
diphenyliodonium trifluoromethanesulfonate,
4-methoxyphenylphenyliodinium hexafluoroantimonate,
4-methoxyphenylphenyliodinium trifluoromethanesulfonate,
bis(4-tert-butylphenyl)iodonium tetrafluoroborate
bis(4-tert-butylphenyl)iodonium hexafluorophosphate,
bis(4-tert-butylphenyl)iodonium hexafluoroantimonate
bis(4-tert-butylphenyl)iodonium trifluoromethanesulfonate,
triphenylsulfonium hexafluorophosphate,
triphenylsulfonium hexafluoroantimonate,
triphenylsulfonium trifluoromethanesulfonate,
triphenylsulfonium adamantanemethoxycarbonyldifluoromethylsulfonate, triphenylsulfonium
1-(3-hydroxymethyladamantane)methoxycarbonyldifluoromethanesulfonate,
triphenylsulfonium 1-(hexahydro-2-oxo-3,5-methano-2H-cyclopenta[b]furan-6-yloxycarbonyl)difluoromethanesulfonate,
triphenylsulfonium 4-oxo-1-adamantyloxycarbonyldifluoromethanesulfonate,
4-methoxyphenyldiphenylsulfonium hexafluoroantimonate,
4-methoxyphenyldiphenylsulfonium trifluoromethanesulfonate,
p-tolyldiphenylsulfonium trifluoromethanesulfonate,
p-tolyldiphenylsulfonium perfluorobutanesulfonate,
p-tolyldiphenylsulfonium perfluorooctanesulfonate,
2,4,6-trimethylphenyldiphenylsulfonium trifluoromethanesulfonate,
4-tert-butylphenyldiphenylsulfonium trifluoromethanesulfonate,
4-phenylthiophenyldiphenylsulfonium hexafluorophosphate,
4-phenylthiophenyldiphenylsulfonium hexafluoroantimonate,
1-(2-naphtholylmethyl)thiolanium hexafluoroantimonate,
1-(2-naphtholylmethyl)thiolanium trifluoromethanesulfonate,
4-hydroxy-1-naphthyldimethylsulfonium hexafluoroantimonate,
4-hydroxy-1-naphthyldimethylsulfonium trifluoromethanesulfonate,
cyclohexylmethyl(2-oxocyclohexyl)sulfonium trifluoromethanesulfonate,
cyclohexylmethyl(2-oxocyclohexyl)sulfonium perfluorobutanesulfonate,
cyclohexylmethyl(2-oxycyclohexyl)sulfonium perfluorooctanesulfonate,
2-oxo-2-phenylethylthiacyclopentanium trifluoromethanesulfonate,
2-oxo-2-phenylethylthiacyclopentanium perfluorobutanesulfonate,
2-oxo-2-phenylethylthiacyclopentanium perfluorooctanesulfonate,
2-methyl-4,6-bis(trichloromethyl)-1,3,5-triazine,
2,4,6-tris(trichloromethyl)-1,3,5-triazine
2-phenyl-4,6-bis(trichloromethyl)-1,3,5-triazine,
2-(4-chlorophenyl)-4,6-bis(trichloromethyl)-1,3,5-triazine,
2-(4-methoxyphenyl)-4,6-bis(trichloromethyl)-1,3,5-triazine,
2-(4-methoxy-1-naphthyl)-4,6-bis(trichloromethyl)-1,3,5-triazine,
2-(benzo[d] [1,3]dioxolan-5-yl)-4,6-bis(trichloromeythyl)-1,3,5-triazine,
2-(4-methoxystyryl)-4,6-bis(trichloromethyl)-1,3,5-triazine,
2-(3,4,5-trimethoxystyryl)-4,6-bis(trichloromethyl)-1,3,5-triazine,
2-(3,4-dimethoxystyryl)-4,6-bis(trichloromethyl)-1,3,5-triazine,
2-(2,4-dimethoxystyryl)-4,6-bis(trichloromethyl)-1,3,5-triazine,
2-(2-methoxystyryl)-4,6-bis(trichloromethyl)-1,3,5-triazine,
2-(4-butoxystyryl)-4,6-bis(trichloromethyl)-1,3,5-triazine,
2-(4-pentyloxystyryl)-4,6-bis(trichloromethyl)-1,3,5-triazine,
1-benzoyl-1-phenylmethyl p-toluenesulfonate (generally called "benzoin tosylate"),
2-benzoyl-2-hydroxy-2-phenylethyl p-toluenesulfonate (generally called α-methylolbenzoin tosylate),
1,2,3-benzene-tri-yl tris(methanesulfonate),
2,6-dinitrobenzyl p-toluenesulfonate,
2-nitrobenzyl p-toluenesulfonate,
4-nitrobenzyl p-toluenesulfonate,
diphenyl disulfone,
di-p-tolyl disulfone
bis(phenylsulfonyl)diazomethane,
bis(4-chlorophenylsulfonyl)diazomethane,
bis(p-tolylsulfonyl)diazomethane,
bis(4-tert-butylphenylsulfonyl)diazomethane,
bis(2,4-xylylsulfonyl)diazomethane,
bis(cyclohexylsulfonyl)diazomethane, (benzoyl)(phenylsulfonyl)diazomethane,
N-(phenylsulfonyloxy)succinimide,
N-(trifluoromethylsulfonyloxy)succinimide,
N-(trifluoromethylsulfonyloxy)phthalimide, N-(trifluoromethylsulfonyloxy)-5-norbornene-2,3-dicarboxyimide,
N-(trifluoromethylsulfonyloxy)naphthalimide,
N-(10-camphorsulfonyloxy)naphthalimide, and the like.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulas:

[3]

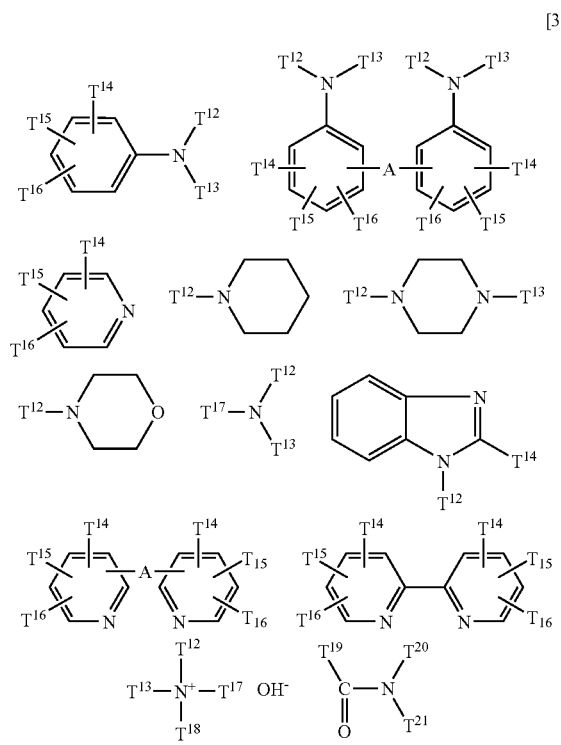

In the formulas, $T^{12}$ and $T^{13}$ each independently represents a hydrogen atom, an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with hydroxyl group, amino group, or alkoxy group having 1 to 6 carbon atoms. At least one hydrogen atom on the amino group may each independently be substituted with alkyl group having 1 to 4 carbon atoms.

$T^{14}$, $T^{15}$ and $T^{16}$ each independently represents a hydrogen atom, an alkyl group, a cycloalkyl group, an aryl group or an alkoxy group. The alkyl group preferably has about 1 to 6 carbon atoms, the cycloalkyl group preferably has about 5 to 10 carbon atoms, the aryl group preferably has about 6 to 10 carbon atoms, and the alkoxy group preferably has about 1 to 6 carbon atoms. Furthermore, at least one hydrogen atom on the alkyl group, cycloalkyl group, aryl group or alkoxy group may each independently be substituted with hydroxyl group, amino group, or alkoxy group having 1 to 6 carbon atoms. At least one hydrogen atom on the amino group may be substituted with alkyl group having 1 to 4 carbon atoms.

$T^{17}$ represents an alkyl group or a cycloalkyl group. The alkyl group preferably has about 1 to 6 carbon atoms, and the cycloalkyl group preferably has about 5 to 10 carbon atoms. Furthermore, at least one hydrogen atom on the alkyl group or cycloalkyl group may each independently be substituted with hydroxyl group, amino group, or alkoxy group having 1 to 6 carbon atoms. At least one hydrogen atom on the amino group may be substituted with alkyl group having 1 to 4 carbon atoms.

In the formulas, $T^{18}$ represents an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with a hydroxyl group, an amino group, or an alkoxy group having 1 to 6 carbon atoms. At least one hydrogen atom on the amino group may each independently be substituted with alkyl group having 1 to 4 carbon atoms.

However, none of $T^{12}$ and $T^{13}$ in the compound represented by the above formula [3] is a hydrogen atom.

A represents an alkylene group, a carbonyl group, an imino group, a sulfide group or a disulfide group. The alkylene group preferably has about 2 to 6 carbon atoms.

Moreover, among $T^{12}$-$T^{18}$, in regard to those which can be straight-chained or branched, either of these may be permitted.

$T^{19}$, $T^{20}$ and $T^{21}$ each independently represents a hydrogen atom, an alkyl group having 1 to 6 carbon atoms, an aminoalkyl group having 1 to 6 carbon atoms, a hydroxyalkyl group having 1 to 6 carbon atoms or a substituted or unsubstituted aryl group having 6 to 20 carbon atoms, or $T^{19}$ and $T^{20}$ bond to form an alkylene group which forms a lactam ring together with adjacent —CO—N—.

Examples of such compounds include hexylamine, heptylamine, octylamine, nonylamine, decylamine, aniline, 2-, 3- or 4-methylaniline, 4-nitroaniline, 1- or 2-naphtylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, imidazole, pyridine, 4-methylpyridine, 4-methylmidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis (2-pyridyl)ethylene, 1,2-bis(4-pyridyl)ethylene, 1,2-bis(2-pyridyloxy)ethane, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "choline"), N-methylpyrrolidone, dimethylimidazole, and the like.

Furthermore, hindered amine compounds having piperidine skeleton as disclosed in JP-A-H11-52575 can be used as quencher.

It is preferable that the present composition contains RESIN in an amount of about 80 to 99.9% by weight and the acid generator in an amount of 0.1 to 20% by weight based on the total amount of RESIN and the acid generator.

When basic compound is used as a quencher, the basic compound is contained preferably in an amount of about 0.001 to 1 part by weight, more preferably in an amount of about 0.01 to 0.3 part by weight based on 100 parts by weight of RESIN.

The present composition can contain, if necessary, various additives in small amount such as a sensitizer, solution suppressing agent, other resins, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethyl Cellosolve acetate, methyl Cellosolve acetate and propylene glycol monomethyl ether acetate; ethers such as di(ethylene glycol) dimethyl ether; esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

Next, novel (meth)acrylic derivatives in the present invention are described as follows.

As a monomer to lead to a structural unit of the formula (I) or (II), a (meth)acrylic derivative of the formula (XII) is preferably used.

In the formula (XII), $X^{11}$ represents a hydrogen atom, a methyl group or a trifluoromethyl group; (1) $R^{11}$ represents a methyl group, $Y^2$ represents a divalent hydrocarbon group which forms an adamantane skeleton together with the adjacent carbon atom, and $Z^7$ represents a methylene group, a trimethylene group or a tetramethylene group, (2) $R^{11}$ represents an ethyl group, an isopropyl group or a butyl group, $Y^2$ represents a divalent hydrocarbon group which forms an adamantane skeleton together with the adjacent carbon atom, and $X^7$ represents a methylene group, an ethylene group, a trimethylene group or a tetramethylene group, or (3) $R^{11}$ represents a methyl group, an ethyl group, an isopropyl group or a butyl group, $Y^2$ represents a tetramethylene group, a pentamethylene group or a divalent hydrocarbon group which forms a norbornane skeleton together with the adjacent carbon atom, and $Z^7$ represents a methylene group, an ethylene group, a trimethylene group or a tetramethylene group.

As a monomer to lead to a structural unit of the formula (V), a (meth)acrylic derivative of the formula (XIII) is preferably used.

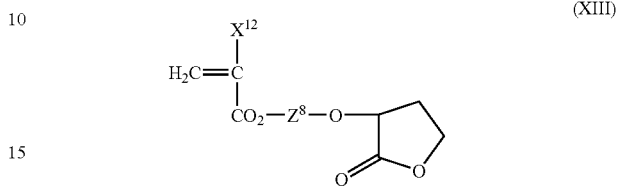

(XIII)

In the formula (XIII), $X^{12}$ represents a hydrogen atom, a methyl group or a trifluoromethyl group, $Z^8$ represents an ethylene group, trimethylene group, a tetramethylene group, a methylcarbonyl group, an ethylcarbonyl group, a propylcarbonyl group or a butylcarbonyl group. As $Z^8$, an ethylene group, a trimethylene group, a methylcarbonyl group, an ethylcarbonyl group and a propylcarbonyl group are preferred.

As a monomer to lead to a structural unit of the formula (IV), a (meth)acrylic derivative of the formula (XIV) is preferably used.

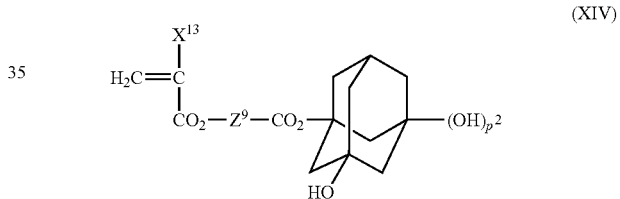

(XIV)

In the formula (XIV), $X^{13}$ represents a hydrogen atom, a methyl group or a trifluoromethyl group, $Z^9$ represents an ethylene group, trimethylene group or a tetramethylene group and p represents 0 or 1. As $Z^9$, an ethylene group and a trimethylene group are preferred.

The (meth)acrylic derivative of the formulas (XII), (XIII) and (XIV) can be produced in the same manner as in the productions of the (meth)acrylic derivatives of the formulas (XXII), (XXVIII) and (XXV) respectively.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

Monomers used in Synthesis Examples are shown as follows:
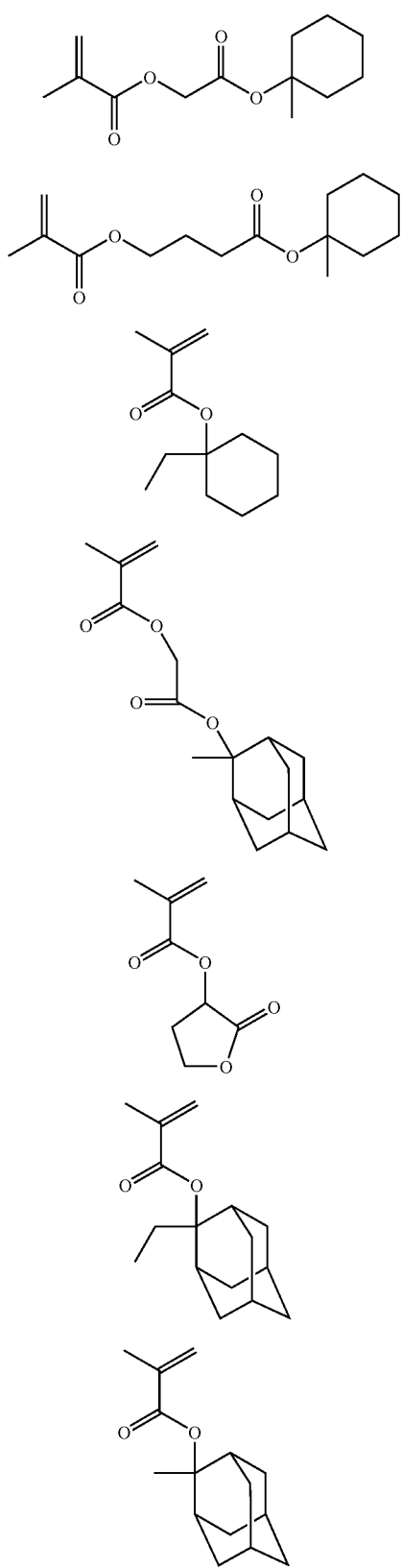
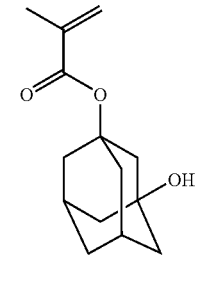
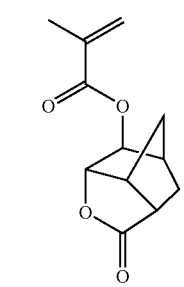
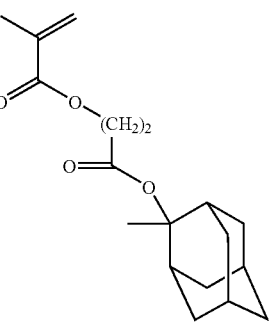
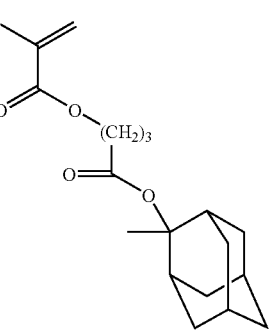
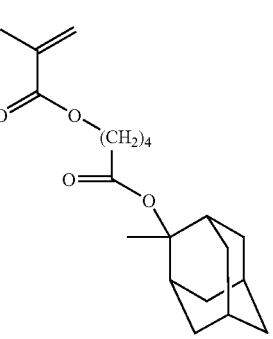

-continued

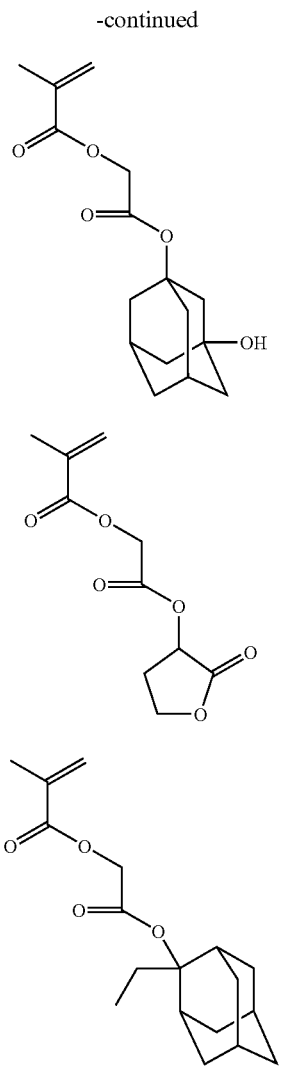

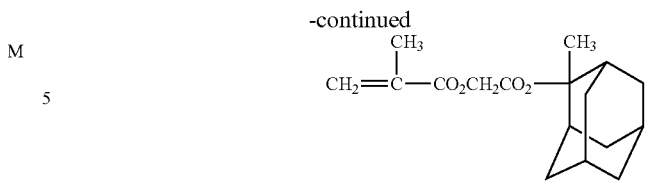

2-Methyladamantanol (27.5 kg) was dissolved in tetrahydrofuran (220 kg), and pyridine was added thereto to form a mixture. After dissolving chloroacetyl chloride (28.02 kg) in tetrahydrofuran (56.04 kg), the solution was added dropwise into the mixture at 40° C. After the addition, the added mixture was maintained a night at the same temperature. The resulting mixture was diluted by iced water, then extracted with ethyl acetate. The organic layer obtained was washed with water, then concentrated to obtain 18.9 kg of chloroester intermediate (Yield: 47.1%.

A solution produced by dissolving the chloroester intermediate (18.9 kg) obtained above in dimethylformamide (37.8 kg) was added dropwise to a slurry consisting of methacrylic acid (10.1 kg), potassium carbonate (16.1 kg), potassium iodide and dimethylformamide (16.1 kg) at a room temperature. After the addition, conventional after-treatments were carried out to obtain oil (19.3 kg), which was identified to be Monomer D described above (Yield: 85.0%).

NMR 1.55~2.04 (12H, adamantyl), 1.64 (s, 3H, methyl), 1.98 (s, 3H methyl), 2.29 (2H, adamantyl), 4.63 (2H, methylene), 5.64 (1H, olefin), 6.22 (1H, olefin) LC-MS 331(M+K)$^+$ ($C_{17}H_{24}O_4$=292.37)

MONOMER SYNTHESIS EXAMPLE 2

Synthesis of
1-(2-ethyl-2-adamantyloxycarbonyl)methyl methacrylate (Monomer O)

MONOMER SYNTHESIS EXAMPLE 1

Synthesis of
1-(2-methyl-2-adamantyloxycarbonyl)methyl methacrylate (Monomer D)

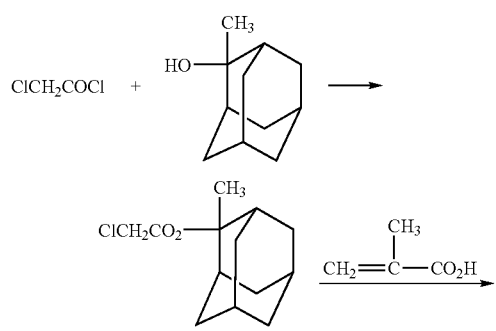

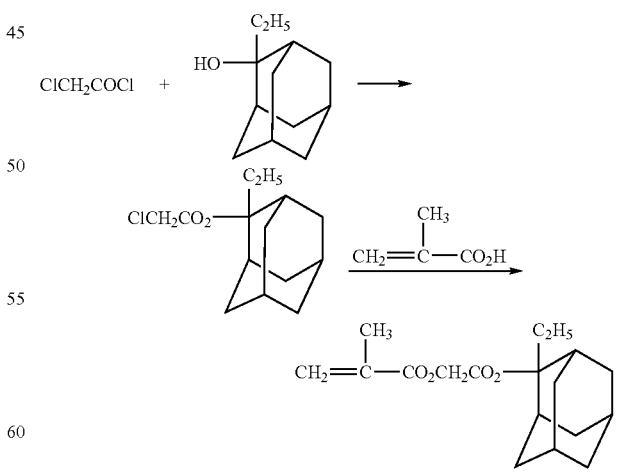

Synthetic experiment was conducted in the same manner as in Monomer Synthesis Example 1 except that 2-ethyl-2-adamantanol was changed to 2-ethyl-2-adamantanol, and Monomer O was obtained.

NMR 0.83 (t, 3H, methyl) 1.57~2.13 (12H, adamantyl), 1.98 (s, 3H, methyl), 2.20 (q, 2H, methylene), 2.37 (2 Hz adamantyl), 4.66 (2H, methylene), 5.64 (1H, olefin), 6.22 (1H, olefin)

MONOMER SYNTHESIS EXAMPLE 3

Synthesis of 1-(1-methyl-1-cyclohexyloxycarbonyl)methyl methacrylate (Monomer A)

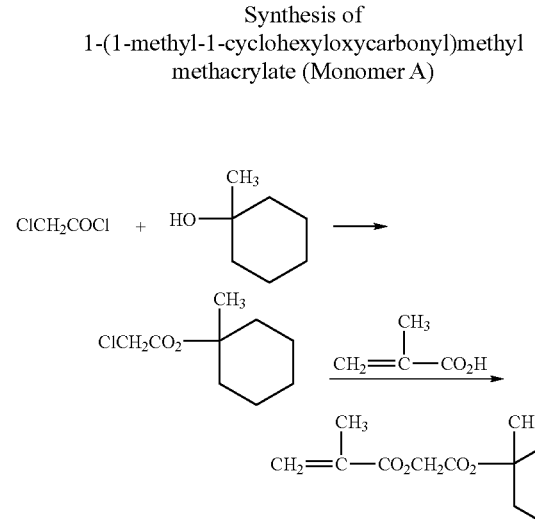

Synthetic experiment was conducted in the same manner as in Monomer Synthesis Example 1 except that 2-ethyl-2-adamantanol was changed to 1-methyl-1-cyclohexanol, and Monomer A was obtained.

NMR 1.50 (s, 3H, methyl) 1.45~1.58 (8H, cyclohexyl), 1.99 (s, 3H, methyl), 2.17 (2H, cyclohexyl), 4.62 (2H, methylene), 5.65 (1H, olefin), 6.22 (1H, olefin)

MONOMER SYNTHESIS EXAMPLE 4

Synthesis of (3-hydroxyadamantyloxycarbonyl)methyl methacrylate (Monomer M)

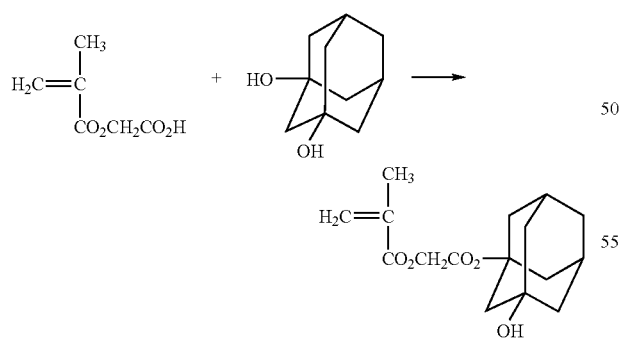

Hydroxycarbonylmethyl methacrylate (30 g) and dihydroxyadamantane (16.8) were added into dichloromethane (500 ml), and p-toluenesulfonic acid (1 g) was added thereto. Then, the mixture was refluxed for 15 hours while removing water generated. After the reaction, conventional after-treatments were carried out to obtain oil (21.2 g), which was identified to be Monomer A described above.

NMR 1.48~2.10 (12H, adamantyl), 1.98 (3H, methyl), 2.32 (2H, adamantyl), 4.583 (2H, methylene), 5.64 (1H, olefin), 6.21 (1H, olefin) LC-MS 333(M+K)$^+$ ($C_{16}H_{22}O_5$=294.34)

MONOMER SYNTHESIS EXAMPLE 5

Synthesis of 3-(1-methyl-1-cyclohexyloxycarbonyl)propyl methacrylate (Monomer B)

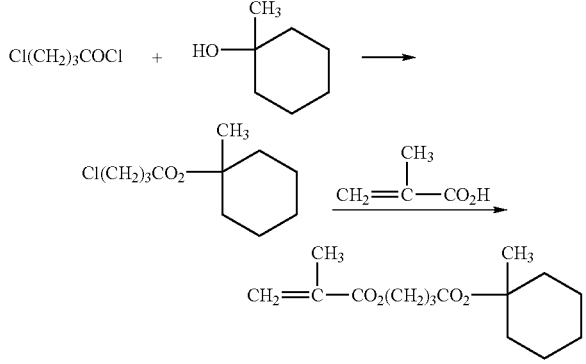

Synthetic experiment was conducted in the same manner as in Monomer Synthesis Example 1 except that 2-ethyl-2-adamantanol and chloroacetyl chloride were changed to 1-methyl-1-cyclohexanol and 4-chlorobutyryl chloride respectively, and Monomer B was obtained.

NMR 1.45~1.58 (8H, cyclohexyl), 1.45 (s, 3H methyl), 1.94 (s, 3H methyl), 1.99 (q, 2H, methylene), 2.15 (2H, cyclohexyl), 2.38 (t, 2H, methylene), 4.18 (t, 2H, methylene), 5.57 (1H, olefin), 6.11 (1H, olefin)

FAB-MS M+=268 ($C_{15}H_{24}O_4$=268.35)

MONOMER SYNTHESIS EXAMPLE 6

Synthesis of 1-(1-ethyl-1-cyclopentyloxycarbonyl)methyl methacrylate

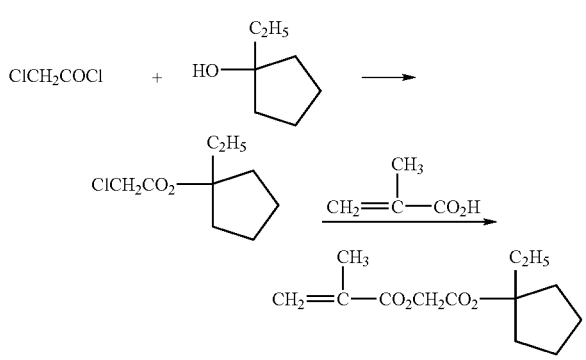

Synthetic experiment was conducted in the same manner as in Monomer Synthesis Example 1 except that 2-ethyl-2-adamantanol was changed to 1-ethyl-1-cyclopentanol, and the above described methacrylic derivative was obtained.

NMR 0.89 (t, 3H, methyl), 1.61-1.68 (6H, cyclopentyl), 1.98 (q, 2H, methylene), 1.99 (t 3H, methyl), 2.12 (2H, cyclopentyl), 4.60 (2H, methylene), 5.64 (1H, olefin), 6.22 (1H, olefin)

MONOMER SYNTHESIS EXAMPLE 7

Synthesis of 3-(1-ethyl-1-cyclopentyloxycarbonyl)propyl methacrylate

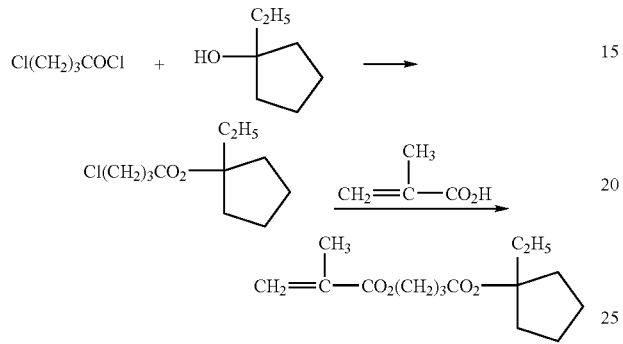

Synthetic experiment was conducted in the same manner as in Monomer Synthesis Example 1 except that 2-ethyl-2-adamantanol and chloroacetyl chloride were changed to 1-ethyl-1-cyclopentanol and 4-chlorobutyryl chloride respectively, and the above described methacrylic derivative was obtained.

NMR 0.88 (t, 3H, methyl), 1.55~1.77 (6H, cyclopentyl), 1.95 (t 3H, methyl), 1.96 (q, 2H, methylene), 1.97 (q, 2H, methylene), 2.11 (2H, cyclopentyl), 2.35 (t, 2H, methylene), 4.15 (t, 2H, methylene), 5.57 (1H, olefin), 6.11 (1H, olefin)

MONOMER SYNTHESIS EXAMPLE 8

Synthesis of 3-(1-ethyl-1-cyclohexyloxycarbonyl)propyl methacrylate

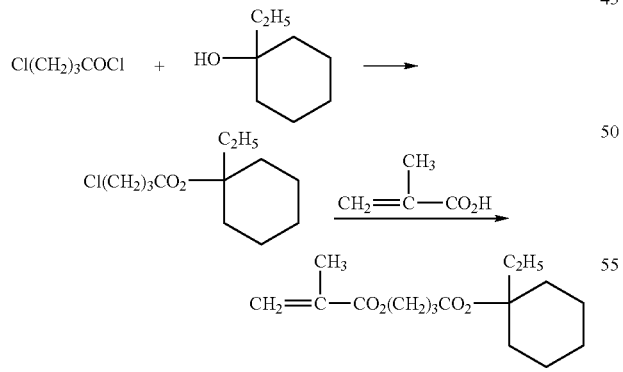

Synthetic experiment was conducted in the same manner as in Monomer Synthesis Example 1 except that 2-ethyl-2-adamantanol and chloroacetyl chloride were changed to 1-ethyl-1-cyclohexanol and 4-chlorobutyryl chloride respectively, and the above described methacrylic derivative was obtained.

NMR 0.83 (t, 3H, methyl), 1.20~1.70 (8H, cyclohexyl), 1.95 (s, 3H, methyl), 1.96 (q, 2H, methylene), 2.00 (m, 2H, methylene), 2.15&2.20 (2H, cyclohexyl), 2.41 (t, 2H, methylene), 4.19 (t, 2H, methylene), 5.57 (1H, olefin), 6.11 (1H, olefin)

MONOMER SYNTHESIS EXAMPLE 9

Synthesis of 4-(1-methyl-1-cyclohexyloxycarbonyl)butyl methacrylate

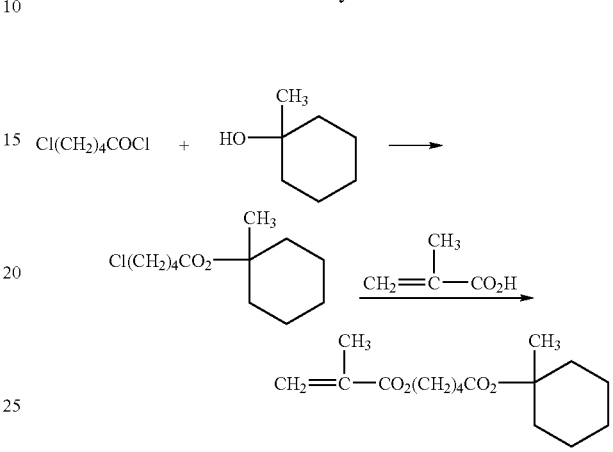

Synthetic experiment was conducted in the same manner as in Monomer Synthesis Example 1 except that 2-ethyl-2-adamantanol and chloroacetyl chloride were changed to 1-methyl-1-cyclohexanol and 5-chlorovaleryl chloride respectively, and the above described methacrylic derivative was obtained.

NMR 1.35~1.58 (8H, cyclohexyl), 1.44 (t+3H, methyl), 1.80 (m, 4H, ethylene), 2.92 (t, 3H, methyl), 2.15 (2H, cyclohexyl), 2.32 (t, 2H, methylene), 4.16 (t, 2H, methylene)% 5.57 (1H, olefin), 6.12 (1H, olefin)

MONOMER SYNTHESIS EXAMPLE 10

Synthesis of 1-(1-ethyl-1-cyclohexyloxycarbonyl)methyl methacrylate

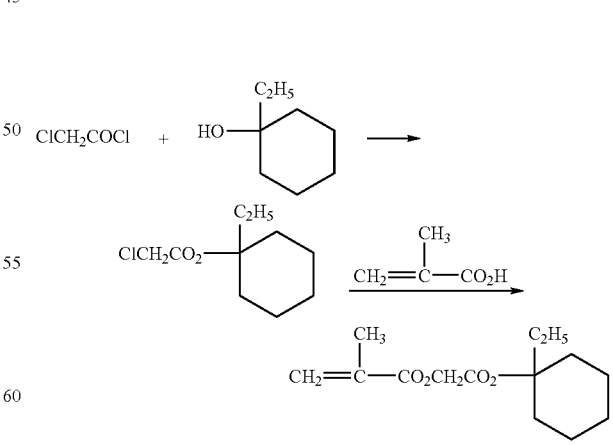

Synthetic experiment was conducted in the same manner as in Monomer Synthesis Example 1 except that 2-ethyl-2-adamantanol was changed to 1-ethyl-1-cyclohexanol, and the above described methacrylic derivative was obtained.

NMR 0.85 (t, 3H, methyl), 1.27~1.71 (8H, cyclohexyl), 1.92 (q, 2H, methylene), 1.99 (t, 3H, methyl), 2.18&2.23 (2H, cyclohexyl), 4.63 (2H, methylene), 5.64 (1H, olefin), 6.22 (1H, olefin)

MONOMER SYNTHESIS EXAMPLE 11

Synthesis of 4-(1-ethyl-1-cyclohexyloxycarbonyl)butyl methacrylate

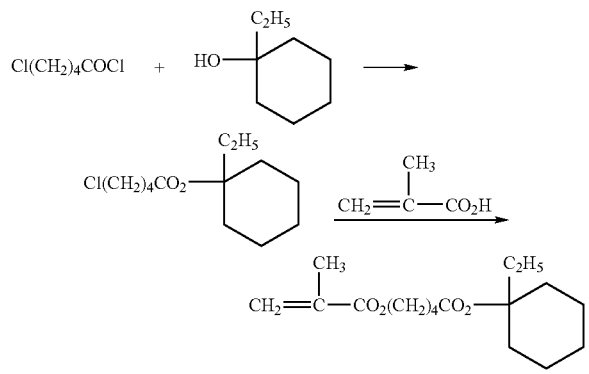

Synthetic experiment was conducted in the same manner as in Monomer Synthesis Example 1 except that 2-ethyl-2-adamantanol and chloroacetyl chloride were changed to 1-ethyl-1-cyclohexanol and 5-chlorovaleryl chloride respectively, and the above described methacrylic derivative was obtained.

NMR 0.82 (t, 3H, methyl), 1.20~1.64 (8H, cyclohexyl), 1.74 (m, 4H, ethylene), 1.89 (q, 2H, methylene), 1.94 (s, 3H, methyl), 2.18&2.24 (2H, cyclohexyl), 2.33 (t, 2H, methylene) 4.19 (t, 2H, methylene), 5.57 (1H, olefin), 6.12 (1H, olefin)

MONOMER SYNTHESIS EXAMPLE 12

Synthesis of 1-(2-methyl-2-norbornyloxycarbonyl)methyl methacrylate

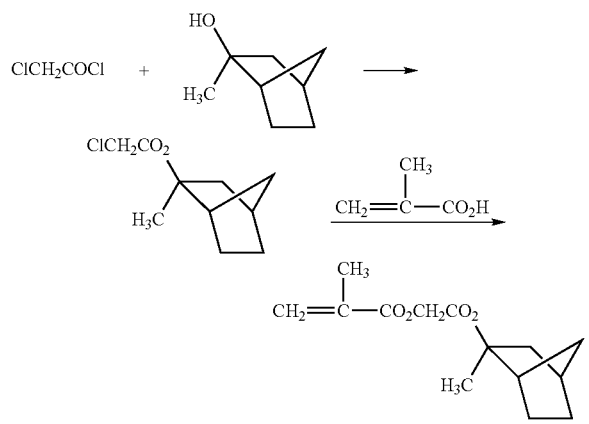

Synthetic experiment was conducted in the same manner as in Monomer Synthesis Example 1 except that 2-ethyl-2-adamantanol was changed to 2-methyl-2-norbornanol, and the above described methacrylic derivative was obtained.

NMR 1.19~1.69 (8H, norbornyl), 1.51 (3H, methyl), 1.98 (3H, methyl), 2.20 (1H, norbornyl), 2.60 (1H, norbornyl), 4.63 (2H, methylene), 5.64 (1H, olefin), 6.22 (1H, olefin)

LC-MS 291(M+K)$^+$ (C$_{14}$H$_{20}$O$_4$=252.31)

MONOMER SYNTHESIS EXAMPLE 13

Synthesis of α-(2-methacryloyloxyethyloxy)-γ-butyrolactone (Monomer N)

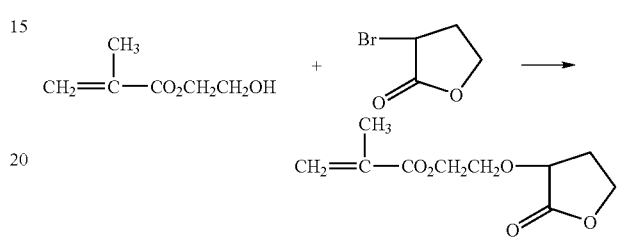

A tetrahydrofuran (70 ml) solution of hydroxyethyl methacrylate was added dropwise into a tetrahydrofuran (30 ml) suspension of sodium hydride (60%; 0.72 g). After stirred for a while, a tetrahydrofuran (30 ml) solution of bromo-γ-butyrolactone was added thereto. The added mixture was stirred at a room temperature for 5 hours. The resulting mixture was after-treated according to the conventional method to obtain oil (9.5 g) which was identified to be Monomer N.

NMR 1.98 (3H, methyl), 2.30~2.38 (1H, lactone), 2.72~2.78 (1H, lactone), 4.30~4.35 (1H, lactone), 4.46~4.50 (1H, lactone), 4.78 (2H, methylene) 5.49 (t, 1H, lactone), 5.69 (1H, lactone), 6.23 (1H, olefin)

LC-MS 267(M+K)$^+$ (C$_{10}$H$_{12}$O$_6$=228.2)

RESIN SYNTHESIS EXAMPLE 1

Into a four-necked flask equipped with a thermometer and condenser, 66.11 parts of 1,4-dioxane was charged and bubbled with nitrogen gas for 30 min. In the nitrogen atmosphere, after the solvent was heated up to 87° C., a solution obtained by mixing 30.0 parts of Monomer D, 12.12 parts of Monomer H, 17.67 parts of Monomer E, 1.01 parts of azobisisobutyronitrile and 57.17 parts of 1,4-dioxane was added dropwise to the heated solvent for 1 hour with maintaining the temperature at 87° C. After the addition, the mixture was maintained at 87° C. for 5 hours. The reaction mixture was poured into a mixed solution of 595 parts of methanol and 66 parts of ion-exchanged water with stirring, the mixture was stirred, then the resin deposited in the mixture was corrected by filtration. The deposit was added to 330 parts of methanol, the mixture was stirred, then the solid was corrected by filtration. The series of operations comprising pouring, stirring and filtration was repeated two more times, and then dried under reduced pressure to obtain polymer having Mw (weight average molecular weight) of 14565 and Mw/Mn of 1.97. This is called resin R7.

RESIN SYNTHESIS EXAMPLES 2 TO 18

Resin synthesis operations were conducted in the same manner as in Resin Synthesis Example 1 except monomers and molar ratio were changed to those described in Table 1, and resins R1 to R6, and R8 to R18 were obtained. the Mw and Mw/Mn values thereof were described in Table 1.

The reaction and after treatments were conducted in the same manner as in Resin Synthesis Example 1 except that monomers given in Table 1 were used in the ratio shown in Table 1 to obtain respective polymers shown in Table 1. Mw, Mw/Mn thereof and the ratio of each of monomers added were shown in Table 1.

TABLE 1

| Resin No. | Monomers & Molar ratio of monomers | Mw | Mw/Mn |
|---|---|---|---|
| R1 | A/F/H/I/E = 20/25/5/20/30 | 9569 | 1.59 |
| R2 | A/F/H/I/E = 30/15/5/20/30 | 10328 | 1.69 |
| R3 | B/F/H/I/E = 20/25/5/20/30 | 12806 | 1.90 |
| R4 | B/F/H/I/E = 10/35/5/20/30 | 8693 | 1.69 |
| R5 | B/F/H/I/E = 5/40/5/20/30 | 8282 | 1.75 |
| R6 | D/F/H/I/E = 20/25/5/20/30 | 9503 | 1.91 |
| R7 | D/H/E = 50/25/25 | 14565 | 1.97 |
| R8 | C/F/H/I/E = 20/25/5/20/30 | 8200 | 1.53 |
| R9 | C/F/H/I/E = 30/15/5/20/30 | 9240 | 1.54 |
| R10 | G/H/E = 50/25/25 | 9721 | 1.53 |
| R11 | J/H/E = 50/25/25 | 11673 | 1.84 |
| R12 | K/H/E = 50/25/25 | 14393 | 2.02 |
| R13 | L/H/E = 50/25/25 | 13391 | 1.86 |
| R16 | O/H/E = 50/25/25 | 11306 | 1.97 |
| R17 | O/I/E = 50/25/25 | 13333 | 2.15 |
| R18 | F/O/H/I/E = 25/20/5/20/30 | 8583 | 2.20 |

EXAMPLES 1 TO 15 AND COMPARATIVE EXAMPLES 1 TO 5

The following components were mixed and dissolved, further, filtrated through a fluorine resin filter having pore diameter of 0.2 μm, to prepare resist liquid.

<Resin>
10 parts of Resin described in Table 1.

<Acid Generator>
S1: (4-methylphenyl)diphenylstilfonium perfluorobutanesulfonate
S2: 1-(2-oxo-2-phenylethyl)tetrahydrothiophenium perfluorobutanesulfonate
S3: tris(4-tert-butylphenyl)sulfonium perfluorooctanesulfonate <Quencher>
Q1: 0.025 part of 2,6-diisopropylaniline
Q2: 0.025 part of tetrabutylammonium hydroxide
Q3: 0.021 part of tetrabutylammonium hydroxide <Solvent>
Kind and amount are described in Table 1.
Y1: 51.5 parts of propylene glycol monomethyl ether acetate, 35.0 parts of 2-heptanone and 3.5 parts of γ-butyrolactone
Y2: 84 parts of propylene glycol monomethyl ether acetate and 4 parts of γ-butyrolactone Silicon wafers were each coated with "ARC-29A-8", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.25 μm after drying. The silicon wafers thus coated with the respective resist liquids were each prebaked on a direct hotplate at temperature shown in "PB" column in Table 2 for 60 seconds. Using an ArF excimer stepper ("NSR ArF" manufactured by Nikon Corporation, NA=0.55 2/3 Annular), each wafer thus formed with the respective resist film was subjected to line and space pattern exposure, with the exposure quantity being varied stepwise.

After the exposure, each wafer was subjected to post-exposure baking on a hotplate at temperature shown in "PEB" column in Table 2 for 60 seconds and then to puddle development for 60 seconds with an aqueous solution of 2.38 wt % tetramethylammonium hydroxide.

In Examples 8 to 15 and Comparative Examples 4 to 6, Reflow Step was added. It was conducted by baking on a hotplate at 165° C. for 60 seconds after the development.

Each of a dark field pattern developed on the organic anti-reflective coating substrate after the development and before and after Reflow Step was observed with a scanning electron microscope, the results of which are shown in Table 3 and Table 4. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Effective Sensitivity:
It is expressed as the amount of exposure that the line pattern (light-shielding layer) and the space pattern (light-transmitting layer) become 1:1 after exposure through 0.13 cm line and space pattern mask and development.

Resolution:
It is expressed as the minimum size of space pattern which gave the space pattern split by the line pattern at the exposure amount of the effective sensitivity.

Line Edge Roughness
When line edge roughness is very good, its evaluation is marked by "⊙".
When line edge roughness is good, its evaluation is marked by "○".
When line edge roughness is bad, its evaluation is marked by "X".

Reflow
When pattern shape is greatly altered before and after Reflow Step, its evaluation is marked by "○".
When only top shape of pattern is altered, its evaluation is marked by "Δ".
When no alteration on pattern is recognized, its evaluation is marked by "X".

TABLE 2

| Example No. | Resin | Acid Generator (kind/amount (part)) | Quencher | Solvent | PB | PEB |
|---|---|---|---|---|---|---|
| Ex. 1 | R1 | S1/0.25 S2/0.2 | Q1 | Y1 | 120° C. | 115° C. |
| Ex. 2 | R2 | S1/0.25 S2/0.2 | Q1 | Y1 | 120° C. | 115° C. |
| Ex. 3 | R3 | S1/0.25 S2/0.2 | Q1 | Y1 | 110° C. | 100° C. |
| Ex. 4 | R4 | S1/0.25 S2/0.2 | Q1 | Y1 | 110° C. | 105° C. |
| Ex. 5 | R5 | S1/0.25 S2/0.2 | Q1 | Y1 | 110° C. | 105° C. |
| Ex. 6 | R6 | S1/0.25 S2/0.2 | Q1 | Y1 | 125° C. | 105° C. |
| Ex. 7 | R7 | S1/0.25 S2/0.2 | Q1 | Y1 | 120° C. | 120° C. |

TABLE 2-continued

| Example No. | Resin | Acid Generator (kind/amount (part)) | Quencher | Solvent | PB | PEB |
|---|---|---|---|---|---|---|
| Ex. 8 | R4 | S1/0.25 S2/0.2 | Q1 | Y1 | 120° C. | 110° C. |
| Ex. 9 | R7 | S1/0.23 S2/0.27 | Q2 | Y2 | 130° C. | 115° C. |
| Ex. 10 | R11 | S1/0.30 | Q1 | Y1 | 100° C. | 100° C. |
| Ex. 11 | R12 | S1/0.30 | Q1 | Y1 | 85° C. | 85° C. |
| Ex. 12 | R13 | S1/0.30 | Q1 | Y1 | 85° C. | 85° C. |
| Ex. 13 | R16 | S1/0.30 | Q1 | Y1 | 90° C. | 85° C. |
| Ex. 14 | R17 | S1/0.30 | Q1 | Y1 | 85° C. | 85° C. |
| Ex. 15 | R18 | S1/0.30 | Q1 | Y1 | 100° C. | 100° C. |
| Comp. Ex. 1 | R8 | S1/0.25 S2/0.2 | Q1 | Y1 | 120° C. | 115° C. |
| Comp. Ex. 2 | R9 | S1/0.25 S2/0.2 | Q1 | Y1 | 120° C. | 115° C. |
| Comp. Ex. 3 | R10 | S1/0.25 S2/0.2 | Q1 | Y1 | 120° C. | 120° C. |
| Comp. Ex. 4 | R10 | S1/0.23 S2/0.27 | Q3 | Y2 | 130° C. | 130° C. |
| Comp. Ex. 5 | R8 | S1/0.25 S2/0.2 | Q1 | Y1 | 120° C. | 110° C. |
| Comp. Ex. 6 | R10 | S1/0.30 | Q1 | Y1 | 130° C. | 125° C. |

TABLE 3

| Example No. | Effective Sensitivity (mJ/cm$^2$) | Resolution (μm) | Line Edge Roughness |
|---|---|---|---|
| Ex. 1 | 61 | 0.12 | ⊚ |
| Ex. 2 | 67 | 0.13 | ⊚ |
| Ex. 3 | 63 | 0.13 | ⊚ |
| Ex. 4 | 80 | 0.13 | ○ |
| Ex. 5 | 74 | 0.13 | ○ |
| Ex. 6 | 95 | 0.13 | ⊚ |
| Ex. 7 | 60 | 0.14 | ⊚ |
| Ex. 10 | 60 | 0.12 | ⊚ |
| Ex. 11 | 65 | 0.13 | ⊚ |
| Ex. 12 | 57.5 | 0.12 | ⊚ |
| Ex. 13 | 40 | 0.13 | ⊚ |
| Ex. 14 | 52.5 | 0.13 | ⊚ |
| Ex. 15 | 60 | 0.12 | ⊚ |
| Comp. Ex. 1 | 57 | 0.13 | Δ |
| Comp. Ex. 2 | 55 | 0.12 | ○ |
| Comp. Ex. 3 | 102.5 | 0.15 | Δ |
| Comp. Ex. 6 | 60 | 0.13 | Δ |

Apparent from the results shown in Table 3, while keeping equivalent or greater effective sensitivity and resolution, patterns obtained by Examples 1 to 7 and 10 to 15 which correspond to the present invention show better line edge roughness than those of Comparative Examples 1 to 3 and 6.

TABLE 4

| Example No. | Effective Sensitivity (mJ/cm$^2$) | Resolution** (μm) | Reflow |
|---|---|---|---|
| Ex. 8 | 51 | 0.13 | ○ |
| Ex. 9 | 44 | 0.15 | ○ |
| Ex. 10 | 60 | 0.12 | ○ |
| Ex. 11 | 65 | 0.13 | ○ |
| Ex. 12 | 57.5 | 0.12 | ○ |
| Ex. 13 | 40 | 0.13 | ○ |
| Ex. 14 | 52.5 | 0.13 | ○ |
| Ex. 15 | 60 | 0.12 | ○ |

TABLE 4-continued

| Example No. | Effective Sensitivity (mJ/cm$^2$) | Resolution** (μm) | Reflow |
|---|---|---|---|
| Comp. Ex. 4 | 41 | 0.14 | X |
| Comp. Ex. 5 | 52.5 | 0.14 | Δ |
| Comp. Ex. 6 | 60 | 0.13 | X |

**Resolution after the development

Apparent from the results shown in Table 4, while keeping equivalent or greater effective sensitivity and resolution, patterns obtained by the resist composition of Examples 8 to 15 which correspond to the present invention can be made finer by Reflow Step compared with those obtained by the resist compositions of Comparative Examples 4 to 6.

The chemically amplified positive resist composition of the present invention is suitable for excimer laser lithography using ArF, KrF and the like, and gives excellent resolution and sensitivity to resist pattern and excellent pattern shape and particularly, gives excellent line edge roughness. Moreover, the resist composition makes it possible to give finer pattern by Reflow Step.

What is claimed is:

1. A chemically amplified positive resist composition comprising
   (A) a resin which comprises
   (i) a structural unit of the formula (IX)

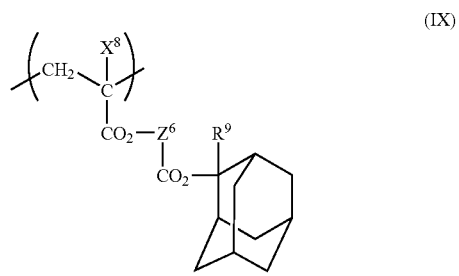

(IX)

wherein $X^8$ represents a hydrogen atom, an alkyl group having 1 to 4 carbon atoms or a perfluoroalkyl group having 1 to 4 carbon atoms, $Z^6$ represents a methylene group, an ethylene group, a trimethylene group or a tetramethylene group, and $R^9$ represents an alkyl group having 1 to 4 carbon atoms, and (ii) a structural unit of the formula (VIII)

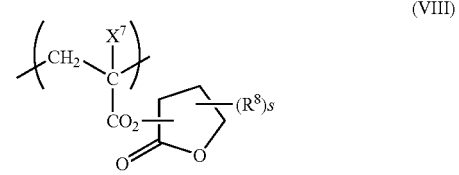

(VIII)

wherein $X^7$ represents a hydrogen atom, an alkyl group having 1 to 4 carbon atoms or a perfluoroalkyl group having 1 to 4 carbon atoms, $R^8$ represents an alkyl group having 1 to 4 carbon atoms or an alkoxy group having 1 to 4 carbon atoms, s represents an integer of 0 to 2, and (B) an acid generator, wherein the acid generator is triphenylsulfonium 1-(3-hydroxymethyl-adamantane)methoxycarbonyldifluoromethanesulfonate, triphenylsulfonium 1-(hexahydro-2-oxo-3,5-methano-2H-cyclopenta[b]furan-6-yloxycarbonyl)difluoromethanesulfonate or triphenylsulfonium 4-oxo-1-adamantyloxycarbonyldifluoromethanesulfonate.

2. The composition according to claim 1, wherein the structural unit of the formula (IX) is a structural unit of the formula (X)

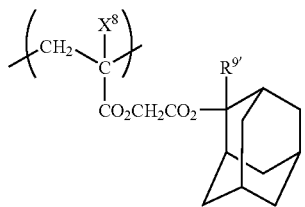

(X)

wherein $X^8$ represents a hydrogen atom or a methyl group, and $R^{9'}$ represents a methyl group, an ethyl group, isopropyl group or a butyl group, and the structural unit of the formula (VIII) is a structural unit of the formula (VIII')

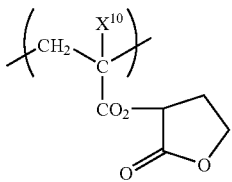

(VIII')

wherein $X^{10}$ represents a hydrogen atom or a methyl group.

* * * * *